US007147837B2

(12) United States Patent
Lauffer et al.

(10) Patent No.: US 7,147,837 B2
(45) Date of Patent: Dec. 12, 2006

(54) BIOACTIVATED DIAGNOSTIC IMAGING CONSTRAST AGENTS

(75) Inventors: Randall B. Lauffer, Brookline, MA (US); Thomas J. McMurry, Winchester, MA (US); Stephen O. Dunham, Madison, NJ (US); Daniel M. Scott, Acton, MA (US); David J. Parmelee, Belmont, MA (US); Stéphane Dumas, Cambridge, MA (US)

(73) Assignee: Epix Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/758,729

(22) Filed: Jan. 16, 2004

(65) Prior Publication Data

US 2004/0156785 A1 Aug. 12, 2004

Related U.S. Application Data

(63) Continuation of application No. 09/952,971, filed on Sep. 14, 2001, now Pat. No. 6,709,646, which is a continuation of application No. 08/823,643, filed on Mar. 25, 1997, now abandoned.

(60) Provisional application No. 60/014,448, filed on Apr. 1, 1996.

(51) Int. Cl.
*A61K 51/00* (2006.01)
*A61M 36/14* (2006.01)

(52) U.S. Cl. .................. 424/1.65; 424/1.69; 534/15

(58) Field of Classification Search .............. 424/9.36, 424/9.364, 9.365, 1.65, 1.69, 1.11; 534/7, 534/10–16
See application file for complete search history.

(56) References Cited

U.S. PATENT DOCUMENTS

| 4,880,008 | A | 11/1989 | Lauffer |
| 4,899,755 | A | 2/1990 | Lauffer et al. |
| 5,094,848 | A | 3/1992 | Brixner |
| 5,171,563 | A | 12/1992 | Abrams et al. |
| H1312 | H | 5/1994 | Coughlin et al. |
| RE35,524 | E | 6/1997 | Saulnier et al. |
| 5,707,605 | A | 1/1998 | Meade et al. |
| 5,783,662 | A | 7/1998 | Janmey et al. |
| 5,932,188 | A | 8/1999 | Snow et al. |

FOREIGN PATENT DOCUMENTS

| DE | 19507822 | 8/1996 |
| EP | 264333 | 4/1998 |
| WO | WO 91/03200 | 3/1991 |
| WO | WO 95/15306 | 6/1995 |
| WO | WO 95/15319 | 6/1995 |
| WO | WO 96/23526 | 8/1996 |
| WO | WO 96/38184 | 12/1996 |

OTHER PUBLICATIONS

Allen et al., "Liposomes containing synthetic lipid derivatives of poly (ethylene glycol) show prolonged circulation half-lives in vivo," *Biochim. Biophys. Acta*, 1991, 1066:29-36.
Blau, "Radiotracers for Functional Brain Imaging," *Seminars in Nuclear Medicine*, vol. XV, No. 4 (Oct. 1985).
Brechbiel et al., "Synthesis of 1-(*p*-Isothiocyanatobenzyl) Derivatives of DTPA and EDTA. Antibody Labeling and Tumor-Imaging Studies," *Inorg. Chem.*, 1986, 25:2772-2781.
Cacheris et al., "The Relationship between Thermodynamics and the Toxicity of Gadolinium Complexes," *Mag. Res. Imag.*, 1990, 8:467-481.
Carter and Ho, "Structure of Serum Albumin," *Adv. Protein Chem.*, 1994, 45:153-203.
Chan et al., "In vitro studies on the Hypoxic Retention of a Novel Technetium—99m Labeled Nitroimidazole in Rat Heart," *J. Nuclear Med.*, 1994, 35:18P, Abstract No. 65.
Chu, "The Quantitative Analysis of Structure-Activity Relationships," *Burger's Medicinal Chemistry*, Part 1, 1980, 4th ed., pp. 393-418.
Cox et al., "Synthesis of C- and N- Functionalised Derivatives of 1,4,7—Triazacyclonon-ane-1,4,7-triyltriacetic acid (NOTA), 1,4,7,10—Tetra-azacycoldodecane-1,4,7,10—tetrayltetra-acetic Acid (DOTA), and Diethylenenetriaminepenta-acetic Acid (DTPA): Bifunctional Complexing Agents for the Derivatisation of Antibodies," *J. Chem. Soc. Perkin Transactions I*, 1990, pp. 2567-2576.
Green et al., "Protection for the Hydroxyl Group, including 1,2- and 1,3-Diols," *Protective Groups in Organic Synthesis*, 1981 2nd ed., J. Wiley & Sons, pp. 10-86.
Harris et al., "Ferric Ion Sequestering Agents. 6. The Spectrophotometric and Potentiometric Evaluation of Sulfonated Tricatecholate Ligands," *J. Am. Chem. Soc.*, 1981, 103:2667.
Harris et al., "Spectrophotometric Determination of the Proton-Dependent Stability Constant of Ferric Enterobactin," *J. Am. Chem. Soc.*, 1979, 101:2213.
He and Carter, "Atomic Structure and Chemistry of Human Serum Albumin," *Nature*, 1992, 358:209-215.
Hoey and Smith, "Chemistry of X-Ray Contrast Media," *Radiocontrast Agents*, 1984, Springer-Verlag, NY, Chapter 1, pp. 23-125.
Horrocks and Albin, "Lanthanide Ion Luminescence in Coordination Chemistry and Biochemistry," *Progr. Inorg. Chem.*, 1984, 31:1-104.

(Continued)

*Primary Examiner*—Dameron L. Jones
(74) *Attorney, Agent, or Firm*—Fish & Richardson P.C.

(57) ABSTRACT

The present invention relates to improved diagnostic agents for Magnetic Resonance Imaging and optical imaging. In particular, this invention relates to MRI and optical imaging agents that allow for the sensitive detection of a specific bioactivity within a tissue. These agents are prodrug contrast agents which are bioactivated in vivo in the presence of the specific bioactivity. This invention also relates to pharmaceutical compositions comprising these agents and to methods of using the agents and compositions comprising the agents.

24 Claims, No Drawings

OTHER PUBLICATIONS

Kragh-Hansen, "Molecular Aspects of Ligand Binding to Serum Albumin," *Pharm. Rev.*, 1981, 33:17-53.

Kumar et al., "Equilibrium and Kinetic Studies of Lanthanide Complexes of Marcrocyclic Polyamino Carboxylates," *Inorg. Chem.*, 1993, 32:587-593.

Lauffer, "Paramagnetic Metal Complexes as Water Proton Relaxation Agents for NMR Imaging: Theory and Design," *Chemical Reviews*, 1987, 87:901-927.

Leo, "Partition Coefficients and their Uses," *Chemical Reviews*, 1971, 71:525-616.

March, *Advanced Organic Chemistry: Reactions, Mechanisms, and Structure*, 1992, 4th ed., J. Wiley & Sons, pp. 392-396.

McMurry et al., "Convenient Synthesis of Bifunctional Tetraaza Macrocycles," *Bioconjugate Chemistry*, 1992, 3:108-117.

Okezaki et al., "Structure-Tissue Distribution Relationship Based on Physiological Pharmacokinetics for NY-198, A New Antimicrobial Agent, and the Related Pyridonecarboxylic Acids," *Drug Metabolism and Disposition*, 1988, 16:865-874.

Paphadjopoulos et al., "Sterically Stabilized Liposomes: Improvements in Pharmacokinetics and Antitumor Therapeutic Efficacy," *Proc. Natl. Acad. Sci. USA*, 1991, 88:11460-11464.

Roda et al., "Quantitative Aspects of the Interaction of Bile Acids with Human Serum Albumin," *J. Lipid Research*, 1982, 23:490-495.

Rolinson and Sutherland, "The Binding of Antibiotics to Serum Proteins," *British J. Pharmacol.*, 1965, 25:638-650.

Schumhmann-Giampieri et al., "Preclinical Evaluation of Gd-EOB-DTPA as a Contrast Agent in MR Imaging of the Hepatobiliary System," *Radiology*, 1992, 183:59-64.

Tinoco et al., "Equilibrium Dialysis and Scatchard Plots,' *Physical Chemistry: Principles and Applications in Biological Sciences*, 1985, 2nd ed., Prentice-Hall, pp. 172-177.

Villringer et al., "Dynamic Imaging with Lanthanide Chelates in Normal Brain: Contrast Due to Magnetic Susceptibility Effects," *Mag. Res. Med.*, 1988, 6:164-174.

Watson et al., "Contrast Agents in Magnetic Resonance," *Magnetic Resonance Imaging*, 1992, 2nd ed., Mosby-Year Book, Inc., vol. 1, Chapter 14.

Williams and Rappaport, Synthesis of Enantiomerically Pure Diethylenetriaminepentaacetic Acid Analogues. L-Phenylalanine as the Educt for Substitution at the Central Acetic Acid,' *J. Org. Chem.*, 1993, 58:1151-1158.

Wright et al., "Heats and Entropies of Formation of Metal Chelates of Polyamine and Polyaminocarboxylate Ligands," *Anal. Chem.*, 1965, 37:884-892.

BIOACTIVATED DIAGNOSTIC IMAGING CONTRAST AGENTS

CROSS-REFERENCE TO RELATED APPLICATIONS

This application is a Continuation of U.S. patent application Ser. No. 09/952,971, filed Sep. 14, 2001, now U.S. Pat. No. 6,709,646, which is a Continuation of U.S. patent application Ser. No. 08/823,643, filed Mar. 25, 1997, now abandoned, which claims the benefit of U.S. Provisional Application No. 60/014,448, filed Apr. 1, 1996, all of which are incorporated in their entirety herein.

TECHNICAL FIELD OF THE INVENTION

This invention relates to improved diagnostic agents for Magnetic Resonance Imaging (MRI) and optical imaging. These agents permit the sensitive detection of a specific bioactivity within a tissue. This invention also relates to pharmaceutical compositions comprising these agents and to methods of using the agents and compositions comprising the agents.

BACKGROUND OF THE INVENTION

Diagnostic imaging techniques, such as MRI, x-ray imaging, nuclear radiopharmaceutical imaging, ultraviolet/visible/infrared light imaging, and ultrasound imaging, have been used in medical diagnosis for a number of years.

Commonly used contrast materials include organic molecules, metal ions, salts or chelates, particles (particularly iron particles), or labeled peptides, proteins, polymers or liposomes. After administration, these agents may non-specifically diffuse throughout body compartments prior to being metabolized and/or excreted; these agents are generally known as non-specific agents. Alternatively, these agents may have affinity for a particular body compartment, cell, organ, or tissue component; these agents can be referred to as targeted contrast agents.

Contrast agent-enhanced diagnostic imaging procedures desirably increase the contrast between normal and pathological tissue in such a way as to provide two basic classes of information:

1) Detection Data. This includes data necessary to determine whether an abnormality is present in the imaged tissue and the degree to which it is present. The ability to provide this class of information relates to the "sensitivity" of the imaging procedure.

2) Differential Diagnosis Data. This includes data necessary to identify with precision the type of abnormality present. The ability to provide this class of information relates to the "specificity" of the imaging procedure. Specificity is necessary for making an accurate prognosis of the patient's condition and a plan of therapy. For example, although current procedures may be able to detect a tumor, generally they are inadequate to determine whether the tumor is benign or malignant, whether the tumor is likely to metastasize, or whether the tumor is responding to therapy. Such determinations require some knowledge of the specific biochemical state of the tissue.

A number of approaches have been presented to create targeted contrast agents. U.S. Pat. No. 4,880,008, incorporated herein by reference, describes MRI contrast agents which exhibit higher signal, or relaxivity, when they bind non-covalently to serum proteins, such as human serum albumin. For this class of agents, the relaxivity is related to the percent of the contrast agent bound to protein and is typically five to ten times higher than that observed for agents that do not bind proteins. In co-pending U.S. application Ser. No. 08/382,317 (filed Feb. 1, 1995), incorporated herein by reference, blood half life extending moieties ("BHEMs") are added to the protein-binding contrast agents. The resulting agents exhibit enhanced or altered signal for a longer period of time in blood relative to agents lacking the BHEM, rendering these materials especially useful for vascular imaging.

U.S. Pat. No. 4,899,755, incorporated herein by reference, describes MRI contrast agents which are preferentially taken up in normal hepatocytes, resulting in contrast enhancement between normal and abnormal liver tissue.

Another targeting approach is based on conjugation of contrast agents to proteins, antibodies or other biomolecules which are known to interact with cell surface receptors, intracellular receptors, transporters, or other biochemical constituents. See, e.g., U.S. Pat. No. 5,171,563. However, such targeting usually involves a one-to-one interaction between the conjugated agent and the biochemical target, which is often present in relatively low concentrations (frequently nanomolar). Consequently, the number of targeted contrast agent molecules which accumulate in a particular tissue using this approach is limited. For imaging modalities where a significant concentration of agent molecules is often needed for detection (e.g., >1 uM), such as MRI and optical imaging, this "one-to-one" approach is generally too insensitive to be useful.

Attempts to image the biochemical state of tissues include radiopharmaceutical applications, where certain imaging agents are retained in a particular tissue. For example, the positron-emitting $^{18}$F-labeled fluorodeoxyglucose is transported into the brain by passive diffusion, where it is phosphorylated and retained within brain tissue, resulting in an indication of glucose metabolism (see M. Blau, *Seminars in Nuclear Medicine*, Vol. XV, No. 4 (October), 1985). Similarly, a technetium-99m labeled nitroimidazole is reported to be preferentially retained in ischemic heart (see Y.-W. Chan et al., Proceedings of the 41st Annual Meeting of the Society of Nuclear Medicine, Jun. 5-Jun. 8, 1994, *J. Nuclear Medicine* (1994), Volume 35, Abstract No. 65, p. 18P). However, in these cases, the signal from the radiopharmacetical remains constant (i.e., each radioisotope has a characteristic, invariant decay and energy of the particles emitted) and is not affected by either biomodification or preferential retention in a tissue. The specificity and sensitivity of the information which can be obtained by this technique is limited.

There remains a need for contrast agents with improved specificity and sensitivity. In particular, there remains a need for targeted MRI and optical contrast imaging agents that exhibit enough signal enhancement or signal alteration in response to the presence of specific bioactivities to be useful in diagnosing the presence of those bioactivities.

SUMMARY OF THE INVENTION

The present invention provides novel improved diagnostic MRI and optical imaging agents for the sensitive detection of a specific bioactivity within a tissue, and pharmaceutically acceptable derivatives thereof. The imaging agents are prodrug contrast agents which are bioactivated in vivo in the presence of the specific bioactivity. Where the bioactivity is catalytic (e.g., stemming from enzyme activity), a large number of activated contrast agent molecules is generated for every unit of bioactive substance. The bioactivated form of the imaging agent exhibits increased binding affinity for one or more proteins compared to the prodrug, and this change in binding affinity causes a detectable change in the signal characteristics in the imaging agent. This detectable signal change increases the signal (or image) contrast between tissues which contain the targeted bioactivity and those which do not, which thus reflects the presence of the targeted bioactivity.

It is an object of this invention to provide novel compounds that are useful as contrast agents in MRI and optical imaging. It is also an object of this invention to provide pharmaceutical compositions comprising these compounds. It is a further object of this invention to provide methods for using these compounds and compositions comprising them in MRI and optical imaging.

DETAILED DESCRIPTION OF THE INVENTION

In order that the invention herein described may be more fully understood, the following detailed description is set forth.

The novel prodrugs of the present invention are designed with three constraints in mind: 1) they must have one or more specific sites in their structure-that can become modified in vivo by a specific bioactivity; 2) the modified form of the imaging agent generated by this bioactivity must bind to one or more proteins to a greater degree than the prodrug; and 3) the signal characteristics of the imaging agent must be altered when it binds to a protein.

For the present invention, image contrast between normal and abnormal tissue generally requires the bioactivity in one of the tissues to be higher than that in the other. If abnormal tissue expresses a greater concentration of bioactivity than normal tissue, then abnormal tissue will convert more prodrug contrast agent to the activated form than will normal tissue (provided that similar concentrations of prodrug are present in both tissues). In the specific example where increased protein binding by the activated contrast agent generates a more intense signal, the presence of bioactivity results in the image (or signal) being detected as a "hot spot." Conversely, if the abnormal tissue expresses the lesser bioactivity, then abnormal tissue will have a relatively lower concentration of bioactivated contrast agent. In this case, if the increased protein binding by the activated contrast agent generates a more intense signal, the presence of bioactivity results in image (or signal) being detected as a "cold spot."

I. Definitions

Listed below are definitions of terms used to describe the present invention. These definitions apply to the terms as they are used throughout the specification unless otherwise indicated.

The term "aliphatic," as used herein alone or as part of another group, denotes optionally substituted, linear and/or branched chain, saturated or unsaturated hydrocarbons, including alkenyl, alkynyl, cycloalkyl and cycloalkenyl hydrocarbons.

The term "alkyl," as used herein alone or as part of another group, denotes optionally substituted, linear and/or branched chain saturated hydrocarbons.

The terms "alkoxy" or "alkylthio" denote an alkyl group as described above bonded through an oxygen linkage (—O—) or a sulfur linkage (—S—), respectively. The term "alkylcarbonyl," as used herein, denotes an alkyl group bonded through a carbonyl group. The term "alkylcarbonyloxy," as used herein, denotes an alkyl group bonded through a carbonyl group which is, in turn, bonded through an oxygen linkage.

The term "alkenyl," as used herein alone or as part of another group, denotes optionally substituted, straight and branched chain hydrocarbon groups containing at least one carbon to carbon double bond in the chain.

The term "alkynyl," as used herein alone or as part of another group, denotes optionally substituted, straight and branched chain hydrocarbon groups containing at least one carbon to carbon triple bond in the chain.

The term "cycloalkyl," as used herein alone or as part of another group, denotes optionally substituted, saturated cyclic hydrocarbon ring systems.

The term "cycloalkenyl," as used herein alone or as part of another group, denotes such optionally substituted groups as described above for cycloalkyl, further containing at least one carbon to carbon double bond forming a partially unsaturated ring.

The term "aryl," as used herein alone or as part of another group, denotes optionally substituted, homocyclic aromatic groups.

The term "heterocyclic," as used herein alone or as part of another group, denotes optionally substituted fully saturated or unsaturated, aromatic or non-aromatic cyclic groups having at least one heteroatom.

The term "acyl," as used herein alone or as part of another group, denotes the moiety formed by removal of the hydroxyl group from the —COOH group of an organic carboxylic acid.

The term "bioactivity" includes changes in pH; redox potential, concentration of reactive species such as free radicals, or the presence or level of enzymes or biomolecules (including RNA enzymes) that can promote modification or cleavage of one or more bonds in the prodrug. A "bioactivity" can comprise two or more types of biomolecules that together or sequentially cause modification of the prodrug. More than one biomodification can occur to the prodrug (e.g., an enzymatic cleavage followed by simple hydrolysis or decarboxylation).

II. Structure of the Prodrug

The prodrugs of this invention must comprise three domains: an image-enhancing (or signal-generating) moiety ("IEM"), a modification site ("MS"), and a protein binding moiety (PBM).

It is contemplated that the prodrugs of this invention may also comprise a physiologically compatible linker moiety (L) linking the functional domains. In general, L does not contribute significantly to the protein binding or image enhancing functionality of the contrast agent. In some cases, the presence of L may be preferred based on synthetic considerations. In other cases, L may facilitate operation of the bioactivity at the MS. Examples of L's include linear, branched, or cyclic alkyl, aryl, ether, polyhydroxyl, polyether, polyamine, heterocyclic, peptide, peptoid, or other physiologically compatible covalent linkages.

A preferred method of bioactivating the contrast agents of this invention involves enzymatic cleaving of the prodrug at the MS (e.g., by an esterase, proteinase, phosphatase, etc.). In this case, the prodrugs of this invention further comprise a masking moiety (MM). The MM "masks" (or decreases) the binding of the prodrug to the protein within the tissue desired to be imaged; once the MM is removed by cleavage at the MS, then the increased binding affinity of the agent is expressed. In this case, the target or substrate for the bioactivity (e.g., an amide bond) is defined as the MS of the prodrug. This particular method of bioactivation results in the physical separation of at least two molecular fragments, one containing the IEM and PBM, and the other the MM.

The domains of the compounds of this invention can be arranged in a variety of positions with respect to each other. While these domains can exist without any specific boundaries between them (e.g., the MS can be part of the IEM), it is convenient to conceptualize them as separate units of the molecule.

For example, the following structures are contemplated:

(1)

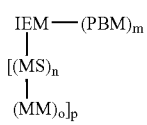

(2)

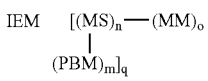

(3)

wherein each of m, n, o, p and q are the same or different, q, n, m and p can be greater than or equal to one, but not zero; and o can be greater than or equal to zero. Generally q, m, n and p are less than five. Most commonly, m, n, p and q are one and o is zero or one.

As used herein, the compounds of this invention are defined to include pharmaceutically acceptable derivatives thereof. A "pharmaceutically acceptable derivative" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species).

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and N—($C_{1-4}$ alkyl)$_4^+$ salts.

The compounds of this invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

The compounds of the present invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

It should be understood that the compounds of this invention may be modified by appending appropriate chemical groups to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

It should also be understood that the compounds of this invention may adopt a variety of conformational and ionic forms in solution, in pharmaceutical compositions and in vivo. Although the depictions herein of specific compounds of this invention are of particular conformations and ionic forms, other conformations and ionic forms of those compounds are envisioned and embraced by those depictions.

Further detailed description of the IEM, PBM, MM, MS moieties is presented below. It should be understood that compounds of this invention are obtained by selecting among the various structures of the moieties taught herein and incorporating them into the final compounds.

A. Image Enhancing Moiety (IEM)

The IEM can be any chemical or substance that provides the signal or contrast in imaging. When the contrast agents of this invention bind to a protein, there is a change in the IEM signal characteristic that is detectable by the external detector. For optical imaging, this can be a change in absorbance, reflectance, fluorescence, an increase or decrease in the number of absorbance peaks or any change in their wavelength maxima, or any other change which by external detection would correspond to a bound IEM. Similarly, for MRI this can be a change in the induced relaxation rates of water protons ($1/T_1$ or $1/T_2$) or any other nearby nuclei, or a shift of one or more peaks or alteration in signal intensity in the NMR spectrum of either the IEM or peaks that appear from nuclei in the binding site for the PBM.

For the purposes of this application, "MRI" is understood to include magnetic resonance spectroscopy techniques. The signals generated by magnetic resonance spectroscopy generally provide information in the form of a chemical shift ($\delta$, in units of ppm) instead of three dimensional images. The chemical shift of a particular nucleus is related to its chemical environment. When a prodrug is bioactivated, the chemical shift of nuclei within the prodrug will be altered.

The IEM can comprise an organic molecule, metal ion, salt or chelate, cluster, particle (particularly iron particle), or labeled peptide, protein, polymer or liposome. For ultraviolet/visible/infrared/fluorescence light (optical) imaging, the IEM can also be any organic or inorganic dye. Particularly useful inorganic dyes include luminescent metal complexes, such as those of Eu(III), Tb(III) and other lanthanide ions (atomic numbers 57–71). See W. Dew. Horrocks & M. Albin, *Progr. Inorg. Chem.* (1984), 31, pp. 1–104.

A particularly useful IEM is a pharmaceutically acceptable metal chelate compound consisting of one or more cyclic or acyclic organic chelating agents complexed to one or more metal ions. Metal ions preferred for optical imaging include those with atomic numbers 13, 21–34, 39–42, 44–50, or 57–83. Paramagnetic metal ions preferred for MRI include those with atomic numbers 21–29, 42, 44, or 57–83.

If the IEM is a metal chelate, the metal chelate should not dissociate to any significant degree during the imaging agent's passage through the body, including a tissue where it may undergo biomodification. Significant release of free metal ions can result in large MRI or optical signal alterations, but may also be accompanied by toxicity, which would only be acceptable in pathological tissues. It is preferred that bioactivation not significantly compromise the stability of the chelate so that the metal complex can remain intact and be excreted. For complexes in which kinetic lability is low, a high thermodynamic stability (a formation constant preferably of at least $10^{15}$ $M^{-1}$ and more preferably at least $10^{20}$ $M^{-1}$) is desirable to minimize dissociation and its attendant toxicity. For complexes in which kinetic lability is comparatively higher, dissociation can be minimized with a lower formation constant, i.e., preferably $10^{10}$ $M^{-1}$ or higher.

Formation constants of known coordination complexes are generally less than $10^{60}$ and more typically in the range of $10^{15}$ to $10^{40}$. Coordination complexes with suitable formation constants include iron enterobactin (formation constant $10^{52}$; W. R. Harris et al., *J. Am. Chem. Soc.* (1981), 103, p. 2667), iron MECAMS (formation constant $10^{41}$; W. R. Harris et al. *J. Am. Chem. Soc.* (1979), 101, p. 2213), gadolinium diethylenetriamine pentaacetic acid ("DTPA") (formation constant $10^{22.46}$; D. L. Wright et al., *Anal. Chem.* (1965), 37, pp. 884–892), gadolinium (1,4,7,10-tetraazacyclotetradecene 1,4,7,10-tetracetic acid ("DOTA") (formation constant $10^{25.3}$; K. Kumar et al., *Inorganic Chemistry* (1993), 32, pp. 587–593), gadolinium DTPA-BMA (formation constant $10^{16.9}$; W. P. Cacheris et al., *Mag. Res. Imag.* (1990), 8 pp. 467–481) and gadolinium EDTA (formation constant $10^{17.3}$; D. L. Wright et al., *Anal. Chem.* (1965) 37, pp. 884–892). Formulations of gadolinium DTPA, DOTA, and DTPA-BMA are used clinically as MRI contrast agents.

Toxicity is also a function of the number of open coordination sites in the complex. The fewer coordination sites, the less tendency there is, generally, for the chelating agent to release the paramagnetic substance. Preferably, therefore, the complex contains two, one or zero open coordination sites. The presence of more than two open sites in general will unacceptably increase toxicity by release of the metal ion in vivo.

In order to effectively enhance MRI images, the complex is preferably capable of enhancing the relaxation rates $1/T_1$ (longitudinal, or spin-lattice) and/or $1/T_2$ (transverse, or spin-spin) of water protons or other imaging or spectroscopic nuclei, including protons, P-31, C-13, Na-23, or F-19 on other biomolecules or injected biomarkers. Relaxivities $R_1$ and $R_2$ are defined as the ability to increase $1/T_1$ or $1/T_2$, respectively, per mM of metal ion; units are $mM^{-1}s^{-1}$. For the most common form of clinical MRI, water proton MRI, relaxivity is optimal where the paramagnetic ion bound to the chelating ligand still has one or more open coordination sites for water exchange. See S. M. Rocklage, et al. "Contrast Agents in Magnetic Resonance", *Magnetic Resonance Imaging*, Second Edition, Volume 1, Chapter 14, (1992), Mosby-Year Book, Inc.; R. B. Lauffer, *Chemical Reviews* (1987), 87, pp. 901–927.

In addition to increasing the $1/T_1$ or $1/T_2$ of tissue nuclei via dipole-dipole interactions, MRI agents can affect two other magnetic properties and thus be of use clinically:

1) an iron particle or metal chelate of high magnetic susceptibility, particularly chelates of Dy, Gd, or Ho, can alter the MRI signal intensity of tissue by creating microscopic magnetic susceptibility gradients. See A. Villringer et al., *Magn. Reson. Med.* (1988), 6, pp. 164–174. No open coordination sites on a chelate are required for this application.

2) an iron particle or metal chelate can also be used to shift the resonance frequency of water protons or other imaging or spectroscopic nuclei, including protons, P-31, C-13, Na-23, or F-19 on the injected agent or the protein to which it binds. Here, depending on the nucleus and strategy used, zero to three open coordination sites may be employed.

The preferred paramagnetic metal is selected from the group consisting of Gd(III), Fe(III), Mn(II) and Mn(III), Cr(III), Cu(II), Dy(III), Tb(III), Ho(III), Er(III) and Eu(III). The most preferred is Gd(III).

The organic chelating ligand should be physiologically compatible. The molecular size of the chelating ligand should be compatible with the size of the paramagnetic metal. Thus gadolinium (III), which has a crystal ionic radius of 0.938A, requires a larger chelating ligand than iron (III), which has a crystal ionic radius of 0.64A.

Many suitable chelating ligands for MRI agents are known in the art. These can also be used for metal chelates for other forms of biological imaging. For MRI imaging, preferred IEMs include:

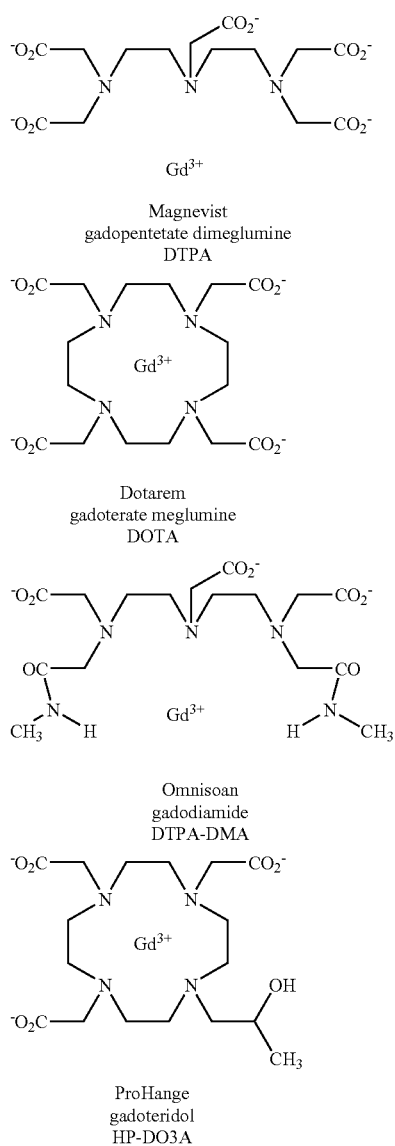

It is known in the art that other metals may be substituted for $Gd^{3+}$ in certain applications.

It is also contemplated that the IEM may comprise a pharmaceutically acceptable salt. Pharmaceutically acceptable salts of this invention include those derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxy-ethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium, magnesium and zinc salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained. The preferred salts of the IEM are the N-methyl-D-glucamine, calcium and sodium salts.

B. Protein Binding Moiety (PBM)

The PBM of the contrast agents of this invention contribute to the binding of the agents to one or more proteins within the tissue containing the bioactivity. This non-covalent binding should be sufficiently tight and the total number of binding sites for the PBM sufficiently large such that contrast is generated between tissues having different levels of targeted bioactivity.

Examples of suitable PBMs include: drugs, lipophilic or amphiphilic organic molecules, porphyrins, receptor ligands, steroids, lipids, hormones, peptides, proteins, oligonucleotides (DNA, RNA or chemically modified versions thereof), antibodies (including monoclonal and genetically engineered versions and their fragments) or other biomolecules or substances known to bind to one or more proteins in the tissue containing the bioactivity desired to be imaged.

Preferred PBMs are those that bind reversibly to proteins in plasma, interstitial space (the fluid between cells), or intracellular space. While any biomolecule or substance that binds to a protein could be used, most useful are those that bind to proteins which either exist in high concentration or have a large number of binding sites for the biomolecule or substance. This affords the ability to temporarily "trap" the large number of modified agents catalytically produced by the bioactivity. The reversible nature of the binding increases the likelihood that the agents will eventually be excreted, a very desirable property for imaging agents.

Examples of preferred proteins are: human serum albumin (HSA) (0.7 mM in plasma, lower concentrations in interstitial space); fatty acid binding protein (FABP; also known as Z-protein or protein A) (roughly 0.1 mM in the primary cells of the liver, kidney, heart and other tissues); glutathione-S-transferase (GST, also known as ligandin), (roughly 0.1 mM in the primary cells of the liver, kidney, heart and other tissues); alpha 1-acid glycoprotein (AAG, MW 41,000) (0.55 g–1.4 g/L) and lipoproteins (concentrated in atherosclerotic plaque). Other preferred examples include the structural proteins of the extracellular matrix (collagens, laminin, elastin, fibronectin, entactin, vitronectin), amyloid (including the beta-2 amyloid protein (A4) of Alzheimer's disease), ceroid (or lipofuscin), and glycoproteins (for example, osteonectin, tenascin, and thrombospondin).

A more preferred protein for positively charged contrast agents or contrast agents containing basic PBMs is alpha 1-acid glycoprotein (AAG). The plasma levels of this positive acute phase protein varies significantly with disease state. For example, the concentrations of AAG increase two to four fold following inflammatory stimuli and plasma levels of AAG have been suggested as a prognostic aid for glioma, metastatic breast and other carcinoma, neonatal infection, and chronic pain. Elevated levels have been noted in atheroscerosis, Chron's disease, myocardial infarction, nephritis, and bacterial, viral, and post-operative infections. Ligands that bind AAG include numerous basic drugs, such as propranolol ($K_a=11.3\times10^5$), imipramine ($K_a=2.4\times10^5$), and chlorpromazine ($K_a=35.4\times10^5$), which can therefore be employed as PBMs.

Ligands for HSA, FABP, and GST are more preferred PBMs since these tend to be neutral with partial negatively charged groups (e.g., an ester, amide, or ketone carbonyl oxygen); such compounds are, in general, less toxic than positively charged molecules. For activated agents designed to bind FABP or GST, hydrophobic long-chain PBMs which mimic the natural ligands (such as palmitic acid), or ring-containing PBMs (such as indocyanine green) are preferred.

Of these three proteins, HSA is highly preferred since ligands for HSA, unlike ligands for FABP and GST, require no intracellular uptake before binding. There need be no intracellular uptake of ligands for HSA since HSA is present in substantial quantities in many extracellular fluid environments including plasma, interstitial space of normal and cancerous tissues, synovial fluid, cerebral spinal fluid and inflammatory or abscess fluid. In many pathologic tissues such as tumors, inflammation, atherosclerotic plaque or the walls of atherosclerotic arteries, capillaries are leaky, resulting in even higher localized HSA levels.

Another reason why HSA is highly preferred is that each protein molecule has a large number of ligand binding sites. See U. Kragh-Hansen, *Pharm. Rev.* (1981), 33, pp. 17–53; X. M. He et al., *Nature* (1992), 358, pp. 209–215; D. C. Carter, *Adv. Protein Chem.* (1994), 45, pp. 153–203.

The design of suitable PBMs is discussed in U.S. Pat. No. 4,880,008 and in U.S. application Ser. No. 08/382,317 (filed Feb. 1, 1995). For binding to HSA, a wide range of hydrophobic or amphiphilic substances function as the PBM. These include but are not limited to aliphatic, alkoxy or alkylthio, alkylcarbonyl, alkylcarbonyloxy, aryl or heterocyclic groups with 1 to 60 carbons and, optionally, one or more nitrogen, oxygen, sulfur, halogen, aliphatic, amide, ester, sulfonamide, acyl, sulfonate, phosphate, hydroxyl or organometallic substituents. Alternatively, the PBM may be a peptide containing hydrophobic amino acid residues and/or substituents with or without hydrophobic or hydrophilic termination groups.

The addition of lipophilic groups into a contrast agent is likely to decrease the solubility of the agent. To retain efficient solubility of the contrast agent at clinically effective dosage levels or higher, it may be preferred to incorporate one or more hydrogen-bonding groups (oxygen, nitrogens, etc.) into the PBM.

While purely aliphatic groups can be used as PBM's, these may not be as preferred as mixed aliphatic-aryl groups or purely aryl groups. Especially when a negative charge is attached to the terminus of long and flexible aliphatic groups, the contrast agents tend to disrupt the interactions between membrane proteins and lipids. This may increase the toxicity of the agent. Thus it is preferred that the PBM contain at least one aryl ring.

In the case of HSA-bound MRI agents for tissue enhancement, it is preferable for the contrast agent to contain two or more lipophilic groups to fully immobilize the agent when bound to the protein. These groups may be on one PBM, or as two or more separate chemical groups attached to the contrast agent. Because of their bulky nature and rigidity, it is highly preferable that the two or more groups each contain an aryl ring, with the two or more rings arranged in a rigid, non-planar orientation.

Preferred PBMs suitable for incorporation into the prodrug contrast agents of this invention include the following structures:

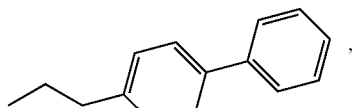 1)

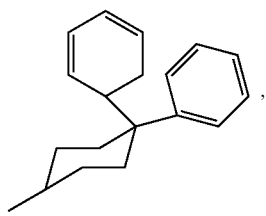 2)

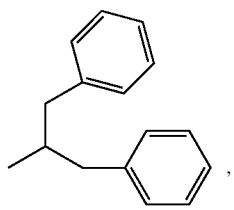 3)

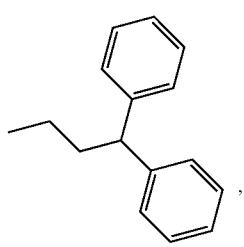 4)

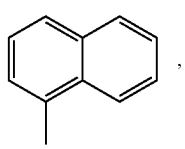 5)

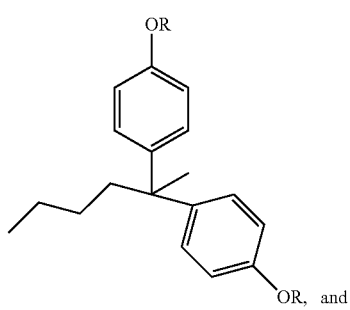 6)

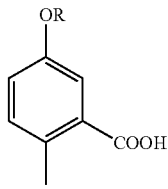 7)

wherein R comprises an aliphatic group and/or at least one aryl ring, or comprises a peptide containing hydrophobic amino acid residues and/or substituents with or without hydrophobic or hydrophilic termination groups.

The magnetic resonance phenomena is complex, and different paramagnetic materials alter the MRI signal to various degrees. See R. B. Lauffer, *Chemical Reviews* (1987), 87, pp. 901–927. A quantitative measurement of the ability of a contrast agent to relax water protons, and consequently affect the MRI image, is provided by its relaxivity. Relaxivity is the dependence of water proton signal intensity upon the concentration of paramagnetic metal ion in solution. Relaxivity is defined as the induced $T_1$ or $T_2$ relaxation per unit time ($R_1$ or $R_2$ in units of $mM^{-1} sec^{-1}$) observed for a contrast agent, where the concentration of the agent is expressed in a millimolar (mM).

The physical properties of a gadolinium complex affect the relaxivity of the contrast agent. The number of water molecules bound to the gadolinium complex, the rate of exchange of the water molecule with bulk solution, the relaxation time of the seven unpaired electrons, and the rotational tumbling time (know as the rotational correlation time) of the contrast agent in solution all contribute to the overall observed relaxivity. Alteration in these physical properties can dramatically alter the relaxivity. For example, the binding of small-molecular-weight gadolinium chelates to large macromolecules slows the rotation tumbling time and increases the relaxation enhancement by factors of 3 to 10. Binding of the contrast agent to the protein causes the magnetic fluctuations between the paramagnetic ion and the water protons to occur on the same time scale as the Larmor frequency, generating the most efficient longitudinal ($T_1$) relaxation possible and the highest possible relaxivity. Thus, non-covalent binding of MRI contrast agents to large macromolecules, such as proteins, is an efficient way to increase the MRI signal. Image contrast is generated between areas which have different levels of non-covalent binding of an activated agent.

To generate bioactivity-related contrast between normal and abnormal tissues, there should be a substantial difference between the protein-binding affinity of the prodrug and that of the bioactivated agent. The prodrug binding affinity is desirably 80% or less of the binding affinity of the activated agent. For example, if the activated agent is 90% bound to a protein within a tissue containing the bioactivity under physiologically relevant conditions (i.e., contrast agent concentration in plasma 0.01–10 mM for MRI and optical imaging), the prodrug should be 72% bound or less under the same conditions. It is preferred that the prodrug exhibit 50% or less of the binding affinity of the activated agent, more preferred is 40% or less, even more preferred is 30% or less, even more preferred is 20% or less, and most preferred is 10% or less.

In MRI, the bioactivity-related contrast between normal and abnormal tissues can be manifested as a change in the induced relaxation rates ($1/T_1$ or $1/T_2$) of water protons, or relaxivities, $R_1$ and $R_2$. In the present invention, the prodrug relaxivity $R_1$ is desirably 80% or less of the $R_1$ of the bioactivated agent. Preferably the prodrug relaxivity $R_1$ is 50% or less of the relaxivity $R_1$ of the bioactivated agent, more preferably 20% or less, and most preferably 10% or less.

Protein binding of contrast agents can be assessed in vitro by equilibrium dialysis or ultrafiltration using a physiologically relevant protein concentration in buffer. See, G. N. Rolinson and R. Sutherland, *British J. Pharmac. Chemother.* (1965), 25, p. 638 (ultrafiltration); D. Glick, *Methods Biochem. Anal.* (1956), 3 p. 265 (equilibrium dialysis). The protein binding measurements set forth in this application are determined by ultrafiltration using 4.5% (w/w) human serum albumin in phosphate buffered saline (0.15 NaCl, 10 mM phosphate, pH 7.4). Preferably at least 10%, and more preferably at least 50%, and even more preferably at least 80%, and most preferably at least 95%, of an activated protein-binding contrast agent will be bound to the protein under physiologically relevant conditions. In this application, the measurement of percent binding of the contrast agent to HSA has an error of approximately +/−5%. Protein binding to other proteins or to serum can be assessed in a similar fashion.

The degree to which an agent has been tuned for maximum relaxivity can be assessed by measuring the relaxivity-bound ($R_1$-bound) in the presence of HSA. This requires measuring the relaxivity of the free chelate ($R_1$-free) as well as the relaxivity ($R_1$-observed) and percent binding of the agent in 4.5% HSA. The $R_1$-observed is a mole fraction weighted average of $R_1$-free and $R_1$-bound:

$R_1$-observed=(fraction-free*$R_1$-free)+(fraction-bound*$R_1$-bound)

Thus:

$$R1\text{-bound} = \frac{[R1\text{-observed} - (\text{fraction-free} * R1\text{-free})]}{\text{fraction-bound}}$$

Protein binding of ligands can also be evaluated theoretically. For a common class of ligands, binding affinity to HSA and other proteins will generally increase with the hydrophobicity of the PBM. Theoretical estimates of the hydrophobicity of a substituent such as a PBM can be obtained by calculating the contribution to the log of the octanol-water (or octanol-buffer) partition coefficient (log P) for the PBM itself using the Hansch n constant for substituents. See A. Leo and C. Hansch, "Partition Coefficients and their Uses," *Chemical Reviews,* 71, pp. 525–616 (1971); K. C. Chu, "The Quantitative Analysis of Structure-Activity Relationships," *Burger's Medicinal Chemistry*, Part 1, pp. 393–418, (4th ed. 1980). Binding affinity will increase with increasing log P contributions. For example, for substituents on aliphatic groups, the following n constants can be used:

| Group | π-aliphatic |
|---|---|
| $CH_3$ | 0.50 |
| Phenyl | 2.15 |

For substituents on aryl groups, the following [1] constants can be used:

| Group | π-aliphatic |
|---|---|
| $CH_3$ | 0.56 |
| $CH_2CH_3$ | 1.02 |
| Phenyl | 1.96 |
| $C(CH_3)_3$ | 1.98 |

Thus, the log P contribution for a p-methylbenzyl group attached to an IEM would be calculated as follows (using the value of the [1]-aliphatic for $CH_3$ as an estimate for the $—CH_2—$ group):

log *P* contribution=0.50+2.15+0.56=3.21

The log P contribution for a p-[4-(t-butyl)-phenyl]benzyl group attached to an IEM would be calculated as follows (using the value of the n-aliphatic for $CH_3$ as an estimate for the —$CH_2$— group)

log $P$ contribution=0.56+2.15+2.15+1.98=6.84

In binding to HSA, a minimum log P contribution of 2 (equivalent to four $CH_3$ groups or one phenyl ring) is required to achieve significant binding. More preferred is a log P contribution of 4 or more. Even more preferred is a log P contribution of 6 or more.

In optical imaging, the invention requires that there be a measurable difference between the optical properties of the non-protein bound prodrug, and the bioactivated protein bound contrast agent. For example, the maximal absorbance of indocyanine green is shifted from 770–780 to 790–805 nm upon binding to proteins in plasma or blood. This difference is used to detect bioactivity by imaging or detecting the protein-bound, activated optical imaging agent. As in the case of MRI, use of a bioactivated prodrug of the optical agent increases the specificity of the agent.

C. Modification Site (MS)

The Modification Site (MS) domain on the prodrug is altered by the specific bioactivity desired to be imaged. That alteration, which is a biotransformation (enzymatic or otherwise) such as bond cleavage, bond formation, oxidation, reduction, or protonation/deprotonation, results in the generation of bioactivated agent. The MS can be an inherent part of the IEM or PBM (as long as it does not adversely affect their individual functions) or it can constitute a separate substituent. One skilled in the art will recognize the chemical structures of the MS which are capable of being altered by the bioactivity.

Preferred MSs are those capable of being altered in vivo by enzymes. Enzymes useful to modify the prodrugs of this invention are those expressed in mammals or in infectious microorganisms (bacteria, yeast, viruses, etc.) which promote modification or cleavage of one or more bonds in the prodrug. The expression of enzyme molecules and their associated in vivo inhibitors is very sensitive to the type of tissue or its condition. Highly preferred modification sites are those which are altered by enzymes which have elevated levels or activity in patients who have inflammatory diseases, infectious disease, cancer, atherosclerosis, thrombosis, myocardial infarction, rheumatoid arthritis, osteoarthritis, endometriosis, periodontal disease, autoimmune disease, and so forth. In the case of enzymatic bioactivity, the MS chemical structure will be closely related to that of the natural or optimal substrates for the enzyme. The natural or optimal substrates are well-known and described in the literature or can be identified by standard biochemical techniques.

Preferred modification sites include those which are cleaved by the EC class of enzymes known as Hydrolases (EC 3.1.*.* through EC 3.99.*.*). These modification sites consist of carbon-oxygen, carbon-nitrogen, phosphorous-oxygen, carbon-carbon and other bonds which are hydrolytically cleaved by the action of the appropriate enzyme. More preferred modification sites include phosphorous-oxygen bonds, which are hydrolysed by enzymes known as phosphatases (EC.3.1.3.*) (Class, Hydrolase; subclass, esterase; sub-subclass, phosphomonoesterase). Specific examples of phosphatase enzymes and their common names are listed in Table I below.

TABLE I

| EC Number | Common Name | Other Names |
| --- | --- | --- |
| EC 3.1.3.1 | Alkaline Phosphatase | Alkaline phosphomonoesterase; phosphomonoesterase; glycerophosphatase |
| EC 3.1.3.2 | Acid Phosphatase | Acid phosphomonoesterase; phosphomonoesterase; glycerophosphatase |

A specific example of a phosphorous-oxygen MS site is that contained in prodrug MRI contrast agent 1. Such phosphate mono-ester derivatives are rapidly hydrolyzed by alkaline phosphatase to generate an alcohol (or phenol) and phosphate ($PO_4^{2-}$) as products. In this specific case, the phosphate mono-ester prodrug 1 binds HSA less strongly than its enzymatic cleavage product, the corresponding alcohol. The clinical relevance of enzymes which act on phosphorous-oxygen MS sites is exemplified by the case of acid phosphatase, which has elevated levels in prostate cancer patients and has been used extensively in the diagnosis, staging and monitoring of prostate cancer for decades.

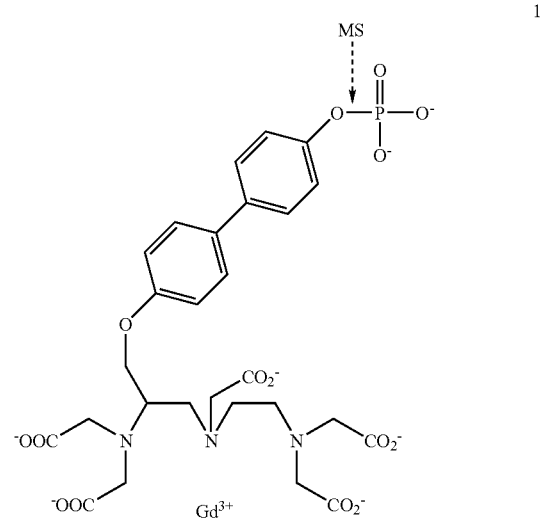

Additional preferred modification sites include those which are cleaved by sulfatases (EC 3.1.6.*; Class, Hydrolase; subclass, esterase; sub-subclass, sulfatase), enzymes which cleave sulfur-oxygen bonds. Steroid sulfatase activity is particularly high in breast tumors, and plays a role in regulating the formation of estrogens within tumors. A listing of sulfatases able to alter sulfate MS sites and their EC numbers are listed in Table II below.

TABLE II

| EC Number | Common Name | Other Names |
| --- | --- | --- |
| EC 2.8.2.4 | Estrone Sulfatase | Estrone Sulfotransferase |
| EC 2.8.2.15 | Steroid sulfotransferase | |
| EC 3.1.6.2 | Steryl-sulfatase | |
| EC 3.1.5.1 | Arylsulfatase | Sulfatase |
| EC 3.1.6.4 | N-acetylgalactosamine-6-sulfatase | |

TABLE II-continued

| EC Number | Common Name | Other Names |
|---|---|---|
| EC 3.1.6.11 | Disulfoglucosamine-6-sulfatase | |
| EC 3.1.6.18 | Glucuronate-2-sulfatase | |
| EC 3.1.6.6 | Choline-sulfatase | |
| EC 3.1.6.8 | Cerebroside-sulfatse | |
| EC 3.1.6.9 | Chondro-4-sulfatase | |
| EC 3.1.6.10 | Chondro-6-sulfatase | |
| EC 3.1.6.12 | N-acetylgalactosamine-4-sulfatase | |
| EC 3.1.6.13 | Iduronate-2-sulfatase | |
| EC 3.1.6.16 | Monomethyl-sulfatase | |
| EC 3.1.6.17 | D-lactate-2-sulfatase | |

Highly preferred MSs are carbon-nitrogen peptide bonds which are hydrolyzed by a subclass of hydrolase enzymes known as proteinases (EC 3.4.*.*). These enzymes hydrolyze an amide bond to form two cleavage products, an amine and a carboxylic acid, one of which remains attached to the bioactivated agent. The MS is designed to mimic a natural or optimal peptide substrate for the specific enzymatic activity to be imaged.

Especially preferred carbon-nitrogen peptide MSs are those which are hydrolyzed by serine proteases (EC 3.4.21.*; Class, Hydrolase; subclass, peptidase, sub-subclass, serine endopeptidase). Serine protease activity has been linked to primary breast cancer, tumor progression that leads to metastasis in breast cancer, the activation of coagulation in patients with lung cancer, pancreatic cancer, severe pancreatitis, and prostate cancer. An MS useful for diagnostic agents for prostate cancer is one which is altered by prostate-specific antigen (PSA), a serine protease glycoprotein (30–34 kDa) produced exclusively by prostatic tissue. PSA exhibits enzymatic activity typical of peptidases chymotrypsin and trypsin, and its physiological substrate appears to be high-molecular-mass seminal vesicle protein (HMM-SV-protein). PSA is extremely useful for monitoring therapy, particularly prostatectomy because its presence is decreased to nearly zero following removal of the prostate. A slow rise in PSA following prostatectomy indicates that either not all of the prostate is removed or that lymph node metastases are present and producing the antigen. The concentration of PSA is also proportional to tumor burden or malignant potential and changes quickly in response to therapy. A listing of specific serine proteases enzymes and their common names are listed in Table III below.

TABLE III

| EC Number | Common Name | Other Names |
|---|---|---|
| EC 3.4.21.77 | Prostate-specific antigen | Semenogelase; PSA; gamma-seminoprotein seminin |
| EC 3.4.21.37 | Leukocyte Elastase | Lysosomal elastase; Neutrophil; elastase; Bone marrow serine protease; Medullasin; |
| EC 3.4.21.36 | Pancreatic Elastase | Pancreato-peptidase E; Pancreatic elastase I |

TABLE III-continued

| EC Number | Common Name | Other Names |
|---|---|---|
| EC 3.4.21.76 | Myeloblastin | Proteinase 3 Wegener's autoantigen |

Preferred MSs are those which are altered by matrix metalloproteinases (MMPs) (EC 3.4.24.*, subclass, peptidase; sub-subclass metalloendopeptidase), enzymes which exhibit high bioactivity in the extracellular space, a tissue compartment which is easily accessible to contrast agents. Furthermore, MMP activity is altered by many diseases. To varying degrees, members of the MMP family are linked to the following diseases: cancer (especially in the degradation of extracellular matrix prior to metastases), atherosclerosis (especially in the degradation of the fibrous cap of atherosclerotic plaque leading to rupture, thrombosis, and myocardial infarction or unstable angina), rheumatoid arthritis and osteoarthritis (destruction of cartilage aggrecan and collagen), periodontal disease, inflammation, autoimmune disease, organ transplant rejection, ulcerations (corneal, epidermal, and gastric), scleroderma, epidermolysis bullosa, endometriosis, kidney disease, and bone disease. Specific metalloproteinase enzymes and their common names are listed in Table IV below.

TABLE IV

| EC Number | Common Name | Other Names |
|---|---|---|
| EC 3.4.24.23 | Matrilysin | MMP-7; Matrin; Uterine metallo-endopeptidase; PUMP-1 |
| EC 3.4.24.7 | Interstitial collagenase | MMP-1; Vertebrate collagenase; Fibroblast collagenase |
| EC 3.4.24.17 | Stromelysin-1 | MMP-3; Transin; Proteoglycanase |
| EC 3.4.24.22 | Stromelysin-2 | MMP-10; Transin-2 |
| EC 3.4.24.24 | Gelatinase | MMP-2; 72-kDa gelatinase; Type IV collagenase; |
| EC 3.4.24.26 | Pseudolysin | Pseudomonas in elastase; *Pseudomonas aeruginosa*-neutral metalloproteinase |
| EC 3.4.24.34 | Neutrophil collagenase | MMP-8 |
| EC 3.4.24.35 | Gelatinase B | MMP-9; 92-kDa gelatinase; Type V collagenase; 92-kDa type IV-collagenase; Macrophage gelatinase |
| EC 3.4.24.39 | Deuterolysin | Penicillium Rogqueforti-protease II; Microbial neutral-proteinase II; Acid metalloproteinase |

In the case where the targeted bioactivity is the enzymatic activity expressed by MMP-1, a matrix metalloproteinase which is elevated in certain inflammatory diseases, a preferred MS is the carbon-nitrogen amide bond linking the amino acids glycine (Gly) and isoleucine (Ile). An example of a prodrug containing a Gly-Ile amide bond MS site is prodrug compound 2.

*[Chemical structure diagram of prodrug compound 2, showing a Gd$^{3+}$ chelate linked through a peptide sequence Gly-Ile-Arg-Lys with the MS site indicated at the Gly-Ile amide bond]*

30

It will be apparent to those skilled in the art that other types of MS (for example, esters, ethers) are hydrolyzed by appropriate target enzymes, such as those categorized as esterases (EC 3.1.*.*) or ether hydrolases (EC 3.3.*.*) and that, based on the knowledge of the chemistry of the target enzyme, optimal MSs may then be incorporated into the prodrug.

In some cases, it is desirable that alteration of the modification site be followed by a second, chemical reaction in order to generate the activated contrast agent. Neutral or negatively charged PBMs are preferred over positively charged PBMs for those agents which are designed to bind HSA (see U.S. Pat. No. 4,880,008). Thus, an especially preferred method for activation of contrast agents that bind to HSA is a secondary chemical reaction which converts positively charged MS cleavage residue to neutral or negatively charged group. This increases the hydrophobicity of the agent (increased log P) and tends to increase HSA binding.

D. Masking Moiety (MM)

When present in a prodrug of this invention, an MM is cleaved from the prodrug when it is bioactivated. An MM can be any organic or inorganic moiety which, when incorporated into the prodrug in a proper position, decreases the protein binding affinity of the prodrug compared to the bioactivated contrast agent.

Examples of suitable MMs include polyethylenegylcol, dextran, hyaluronic acid, or other substances that alter the charge or hydrophobicity of the surface of the PBM. Such materials have been widely used to prevent the interaction large molecular-weight materials (for example, polymers, proteins, or liposomes) with cellular surfaces in the blood. For example, polyethyleneglycol (PEG) attached to liposomes prevents cellular uptake into the reticuloendothelial system, resulting in prolonged circulation of the liposomes. See D. Paphadjopoulos et al., *Proceedings of the National Academy of Sciences* (1991), 88, pp. 11460–11464; T. M. Allen et al., *Biochimica Biophysica Acta* (1991), 1066, pp. 29–36.

For low molecular weight (<5000 Daltons) prodrug contrast agents, hydrophilic and/or charged groups can similarly be used. Such groups can be judiciously positioned within the MM/Linker so that they effectively mask protein binding, yet are released upon bioactivation, thus allowing the increased binding capability of the IEM/PBM to be expressed. For contrast agents which are designed to bind serum proteins such as HSA following bioactivation, hydrophilic and/or charged groups such as hydroxyl, amine (or ammonium), quaternary amine, certain amino acids (especially lysine, arginine, and histidine), sulfoxide, phosphate, sulfate, carboxylate, carbohydrate, sugar, and metal chelates in single or multiple configurations represent potentially effective MMs.

Examples of hydrophilic and/or charged groups which affect HSA binding affinity are described in the art. HSA binding of iodinated x-ray contrast agents is masked by the judicious substitution of hydroxyl groups combined with the elimination of carboxylate groups. For example, the X-ray contrast agent iodipamide binds to HSA with high affinity (>98%), whereas corresponding neutral iodinated x-ray contrast agents, which are modified to contain numerous hydrophilic hydroxyl groups, bind to HSA with low affinity (<1%). See *Radiocontrast Agents*, M. Sovak, ed., Springer-Verlag, New York (1984), Chapter 1 "Chemistry of X-Ray Contrast Media," pp. 23–125. Similarly, a reduction of HSA binding affinity for a series of bile acid derivatives is noted as the number of hydrophilic hydroxyl groups is increased. Thus, lithocholic acid (binding constant=$2.0\times10^5$) binds more tightly than chenodeoxycholic acid cholic and (binding constant=$5.5\times10^4$) which binds more tightly than cholic acid (binding constant=$0.3\times10^4$). See Roda et al., *J. Lipid Research* (1982), 23, pp. 490–495.

Appropriately positioned primary, secondary or tertiary amines have been shown to reduce the HSA binding affinity of certain antibiotics as compared with similar drugs lacking this functionality. This effect is illustrated by data reported for some novel antibiotics, enoxacin and NY-198. See E. Okezaki et al., *Drug Metabolism and Disposition* (1988), 16, pp. 865–74. The fraction of these compounds which were bound to HSA ($f_b$) was reported to be 0.35 and 0.28, respectively, as compared with analogs miloxacin ($f_b=0.86$) and nalidixic acid ($f_b=0.71$) which lacked the amine groups.

Thus, in the preferred prodrugs of this invention, the IEM comprises a DTPA, DOTA, DTPA-BMA or HP-DO3A chelate of $Gd^{3+}$; the PBM comprises one or more of the following structures:

1) 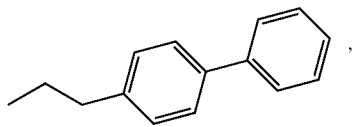

2) 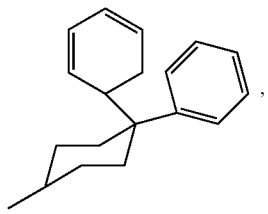

3) 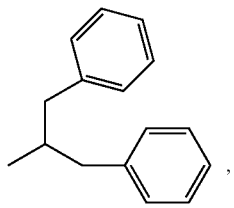

4) 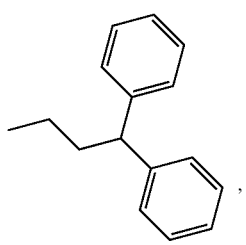

5) 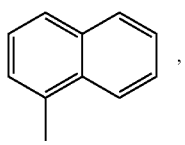

6) 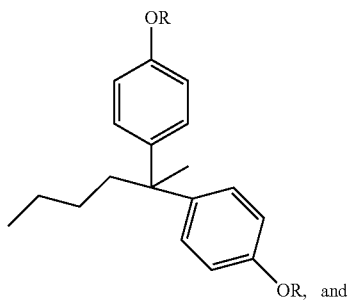
OR, and

7) 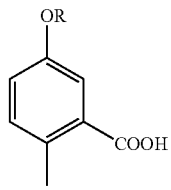

wherein R comprises an aliphatic group and/or at least one aryl ring, or comprises a peptide containing hydrophobic amino acid residues and/or substituents with or without hydrophobic or hydrophilic termination groups; and the MS comprises a bond capable of being altered in vivo by a hydrolase enzyme.

Preferably, the MS is a phosphorus-oxygen bond capable of being hydrolyzed in vivo by a phosphatase enzyme or an amide bond capable of being hydrolyzed in vivo by metalloproteinase enzyme or a serine protease enzyme. Gadolinium complex 1, gadolinium complex 2 and gadolinium complex 10, identified herin, are examples of preferred prodrugs.

III. Synthesis

The compounds of this invention may be synthesized using conventional techniques. Advantageously, these compounds are conveniently synthesized from readily available starting materials. Many starting materials are commercially available, e.g., from Aldrich Chemical Company, Inc., Milwaukee, Wis. Although methods for the syntheses of the compounds of this invention are known to those of ordinary skill in the art of organic synthesis, the following general methods are set forth to illustrate these syntheses. These methods should not be viewed as limiting the scope of this invention in any way.

The synthesis of DTPA and DOTA chelating agents modified with organic substituents used to link the resulting chelate covalently to proteins, including monoclonal antibodies, has been described in the literature. For example, 1-(p-isothiocyanatobenzyl)DTPA was prepared by reacting commercially available p-nitrophenylalanine methyl ester (Aldrich Chemical) with ethylene diamine and subsequent reduction with borane to form the triamine. Alkylation with bromoacetic acid followed by reduction ($H_2$/Pd-C) and reaction with thiophosgene gives the isothiocyanate. See M. W. Brechbiel et al., *Inorganic Chemistry* (1986), 25, pp. 2772–2781. Chelating agents in which the DTPA carbon backbone has been substituted with a aminobutyl group derived from derived from lysine have also been reported. See J. P. L. Cox et al., *J. Chemical Society Perkin Transactions I* (1990), pp. 2567–2576. A synthetic approach to acetate-substituted DTPA molecules via double alkylation of p-nitrophenylalanine has also been described. See M. A. Williams et al., *Journal of Organic Chemistry* (1993), 58, pp. 1151–1158. Similarly, functionalized macrocyclic DOTA molecules have been prepared starting from amino acids and standard cyclization techniques, including Richman-Atkins tosylate chemistry (J. P. L. Cox et al., *J. Chemical Society Perkin Transactions I* (1990), pp. 2567–2576) or high-dilution ring formation (T. J. McMurry et al., *Bioconjugate Chemistry* (1992), pp. 108–117.

The synthesis of hepatobiliary MRI contrast agents containing lipophilic benzyl substituents is described in U.S. Pat. No. 4,899,755. MRI contrast agents containing PBMs and blood half-life extending moieties are described in U.S. application Ser. No. 08/382,317 (filed Feb. 1, 1995). That application describes the synthesis of DTPA chelating agents linked to PBMs through phosphodiester linkages as well as the synthesis of some versatile intermediates, including carbonate hydroxymethyldiethylenetriamine, compound 3, and 1-hydroxymethyl-DTPA-penta-t-butyl ester, compound 4 (Scheme 1).

Other versatile synthetic intermediates for the preparation of prodrug contrast agents include 1-p-hydroxybenzyl-diethylenetriamine (compound 6). See Schumhmann-Giampieri, *G. Radiology* (1992), 183, pp. 59–64. Compound 6 is converted to 1-(p-hydroxybenzyl)-DTPA-penta-t-butyl ester, compound 7, by alkylation with t-butylbromoacetate (Scheme 1).

domains are added to the PBM in a stepwise fashion. For example, a PBM containing a reactive alkyl halide and a second suitably protected reactive group (e.g., hydroxyl or carboxylate) is coupled to the DTPA-penta-t-butyl ester via formation of an ether linkage. Transient protection of reactive groups may be accomplished by means known in the art. See, e.g., Greene, T. W. and Wuts, P. G. M., *Protective Groups in Organic Synthesis*, Second Edition ©1991 John Wiley and Sons, Inc., New York, N.Y. at pp. 10–276. The second reactive group is then deprotected and modified to add the desired MS or both an MS and MM. Final deprotection of the t-butyl ester protecting groups using acid (HCl or TFA) results in the penta acid free ligand, which is then reacted with gadolinium(III) and base to form the gadolinium complex.

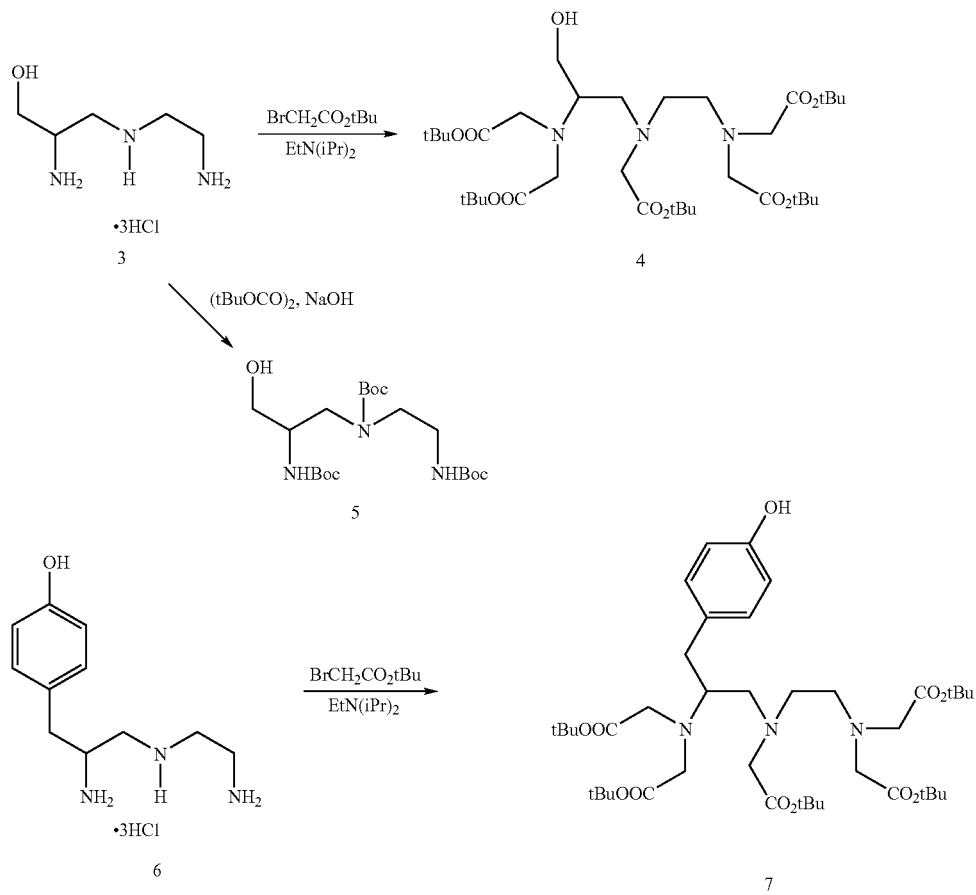

Scheme 1:
Synthetic Intermediates

The carbamate 5 or penta-t-butyl ester intermediates 4 and 7 are derivatized in a single step with PBM groups which incorporate the desired functional domains (MS, MM, L) as well as functional groups which are known in the art to form covalent bonds with hydroxyl or phenol groups (for example, ethers are formed by reaction of alkyl halides with alcohols or by diethyldiazodicarboxylate (DEAD) catalyzed reaction with a second alcohol. See J. March, *Advanced Organic Chemistry*, Third Edition John Wiley & Sons (1995), p.1161 for other appropriate reactions and covalent linkages. Alternatively, the MS and optional MM and/or L As can be appreciated by the skilled artisan, the above synthetic schemes are not intended to comprise a comprehensive list of all means by which the compounds described and claimed in this application may be synthesized. Further methods will be evident to those of ordinary skill in the art.

IV. Use of the Improved Contrast Agents

It is contemplated that pharmaceutical compositions may be prepared comprising any of the prodrugs of the present invention, or pharmaceutically acceptable salts thereof, together with any pharmaceutically acceptable carrier, adjuvant or vehicle. The term "pharmaceutically acceptable carrier, adjuvant or vehicle" refers to a carrier or adjuvant that may be administered to a patient, together with a compound of this invention, and which does not destroy the activity thereof and is nontoxic when administered in doses sufficient to deliver an effective amount of the agent. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, TRIS (tris (hydroxymethyl)amino-methane), partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceuti-cally-acceptable oils, such as olive oil or castor oil, especially in their polyoxyethylated versions. These oil solutions or suspensions may also contain a long-chain alcohol diluent or dispersant.

In some cases, depending on the dose and rate of injection, the binding sites on plasma proteins may become saturated with prodrug and activated agent. This leads to a decreased fraction of protein-bound agent and could compromise its half-life or tolerability as well as the effectiveness of the agent. In these circumstances, it is desirable to inject the prodrug agent in conjunction with a sterile albumin or plasma replacement solution. Alternatively, an apparatus/syringe can be used that contains the contrast agent and mixes it with blood drawn up into the syringe; this is then re-injected into the patient.

The prodrug compounds and pharmaceutical compositions of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term "parenteral" as used herein includes subcutaneous, intravenous, intramuscular, intra-articular, intra-synovial, intrasternal, intrathecal, intrahepatic, intralesional and intracranial injection or infusion techniques.

When administered orally, the pharmaceutical compositions of this invention may be administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, when administered in the form of suppositories for rectal administration, the pharmaceutical compositions of this invention may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

As noted before, the pharmaceutical compositions of this invention may also be administered topically, especially when the target of treatment includes areas or organs readily accessible by topical application, including the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, poly-oxyethylene, polyoxypropylene compound, emulsifying wax and water. Alternatively, the pharmaceutical composi-tions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

For administration by nasal aerosol or inhalation, the pharmaceutical compositions of this invention are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

For intravenous and other types of administration, acceptable dose ranges are between 0.001 and 1.0 mmol/kg of body weight, with the preferred dose of the active ingredient compound being between 0.001 and 0.5 mmol/kg of body weight. Even more preferred is between 0.01 and 0.1 mmol/ kg, and the most preferred dose of the active ingredient compound is between 0.02 and 0.05 mmol/kg.

As the skilled artisan will appreciate, lower or higher doses than those recited above may be required. Specific dosage regimens for any particular patient will depend upon a variety of factors, including the activity of the specific compound employed, the age, body weight, general health status, sex, diet, time of administration, rate of excretion, drug combination and the judgment of the treating physician.

It will be appreciated that the preferred pharmaceutical compositions are those comprising the preferred prodrugs of this invention.

In order that this invention may be better understood, the following examples are set forth. These examples are for purposes of illustration only and are not intended to be construed as limiting the scope of this invention in any manner. In each of the examples, HSA is used as the protein to which bioactivated contrast agent binds.

EXAMPLES

Example Ia

Synthesis of Gadolinium Complex 1

First, carbamate 5 is reacted with the mono-(diallylphosphate) ester of 4,4'-dihydroxybiphenyl in the presence of diethylazodicarboxylate and triphenyl-phosphine to form an ether (Scheme 2). Following deprotection (TFA) and alkylation with bromo-t-butylacetate, the phosphate is deprotected with palladium tetrakis (triphenyl) phosphine. The t-butyl esters are hydrolyzed with trifluoroacetic acid. Reaction with $GdCl_3$ and sodium hydroxide produces the gadolinium complex 1.

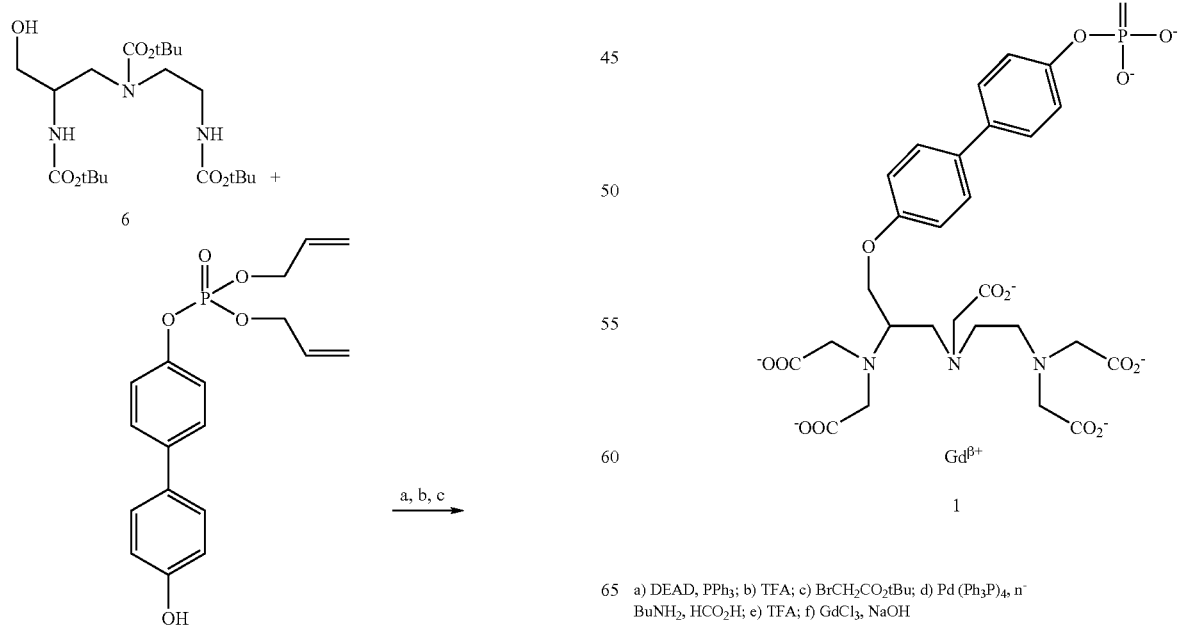

a) DEAD, $PPh_3$; b) TFA; c) $BrCH_2CO_2tBu$; d) Pd $(Ph_3P)_4$, n-$BuNH_2$, $HCO_2H$; e) TFA; f) $GdCl_3$, NaOH

Example Ib

More Preferred Synthesis of Gd Complex 1

First, boronic acid 13 was prepared in three steps from p-bromophenol (Scheme 2a). The phenol was protected as a tert-butyldimethylsilyl ether. Treatment of the arylbromide with butyllithium produced an aryllithium. Reaction of the aryllithium with triisopropyl borate followed by the hydrolysis of borate ester intermediate using mild acidic conditions produces boronic acid 13.

Scheme 2a:
Synthesis of boronic acid 13

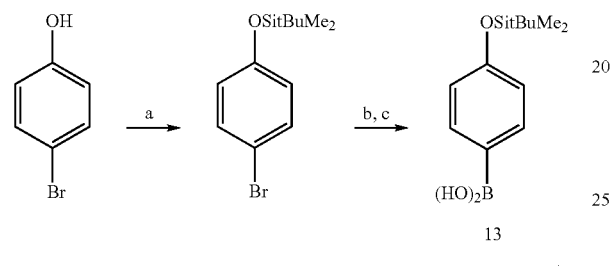

a) tBuMe$_2$SiCl, imidazole, THF; b) nBuLi, -78° C., THF; c) (i-Pro)$_3$B, THF then H$_3$O$^+$ Mitsunobu reaction between the intermediate 5 and bromophenol gave the ether 14. Deprotection of the three BOC groups with trifluoroacetic acid followed by alkylation of the triamine with tert-butyl bromoacetate giving the pentaacetate 15. Tretrakis(triphenylphosphine) palladium-coupling (Suzuki coupling) of the arylbromide 15 with the boronic acid 13 resulted in the biphenyl derivative 16. Hydrolysis of the silyl ether followed by phosphorylation and alkaline hydrolysis of the resulting phosphoryldichoride produced the monophosphate 17. The t-butyl esters were deprotected with trifluoroacetic acid. Reaction with GdCl$_3$ and sodium hydroxide produced the gadolinium complex 1 (Scheme 2b).

Scheme 2b:
More Preferred Synthesis of Gd Complex 1

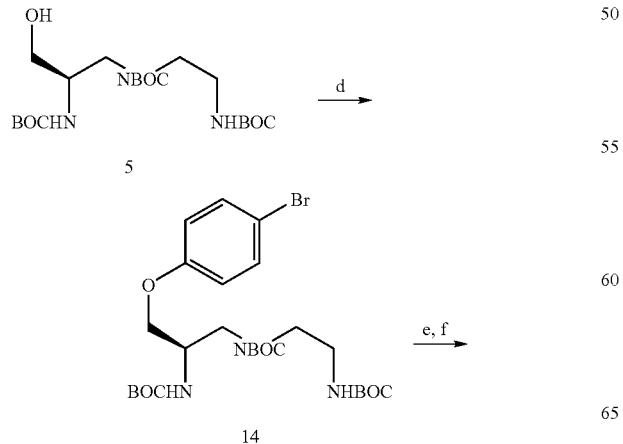

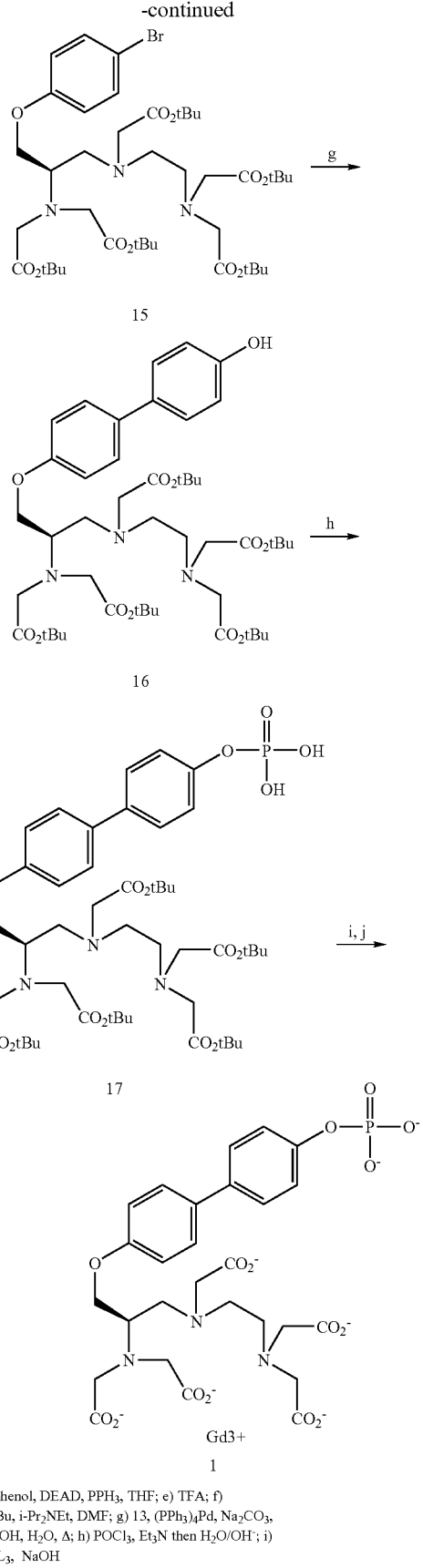

d) p-Bromophenol, DEAD, PPH$_3$, THF; e) TFA; f) BrCH$_2$CO$_2$tBu, i-Pr$_2$NEt, DMF; g) 13, (PPh$_3$)$_4$Pd, Na$_2$CO$_3$, Toluene, MeOH, H$_2$O, Δ; h) POCl$_3$, Et$_3$N then H$_2$O/OH$^-$; i) TFA; j)GdCL$_3$, NaOH

Example IIa

Synthesis of Gadolinium Complex 2

Carbamate 5 is reacted with the methyl-5-bromosalicylate in the presence of diethylazodicarboxylate and triphenylphosphine to form the bromoaryl ether. Tetrakis(triphenylphosphine) palladium-catalyzed coupling of the bromoaryl ether with phenylboronic acid affords the biphenyl ether. Trifluoroacetic acid hydrolysis of the t-butyl carbamates and subsequent alkylation with t-butyl bromoacetate produces the biphenyl ether substituted penta-t-butyl diethylenetriamine pentaacetate. Hydrolysis of the methyl ester with 1 N NaOH in dioxane gives the biphenylcarboxylate, which is coupled with the peptide fragment $H_2$N-gly-ile-arg $(Boc)_2$-lys(Boc)-OtBu using dicyclohexylcarbodiimide in dimethylformamide. Hydrolysis in 6N HCl/dioxane produces the biphenyl peptide substituted diethylenetriamine pentaacetic acid. Reaction with $GdCl_3$ and base gives the gadolinium complex 2 which is purified by reverse-phase HPLC (Scheme 3a).

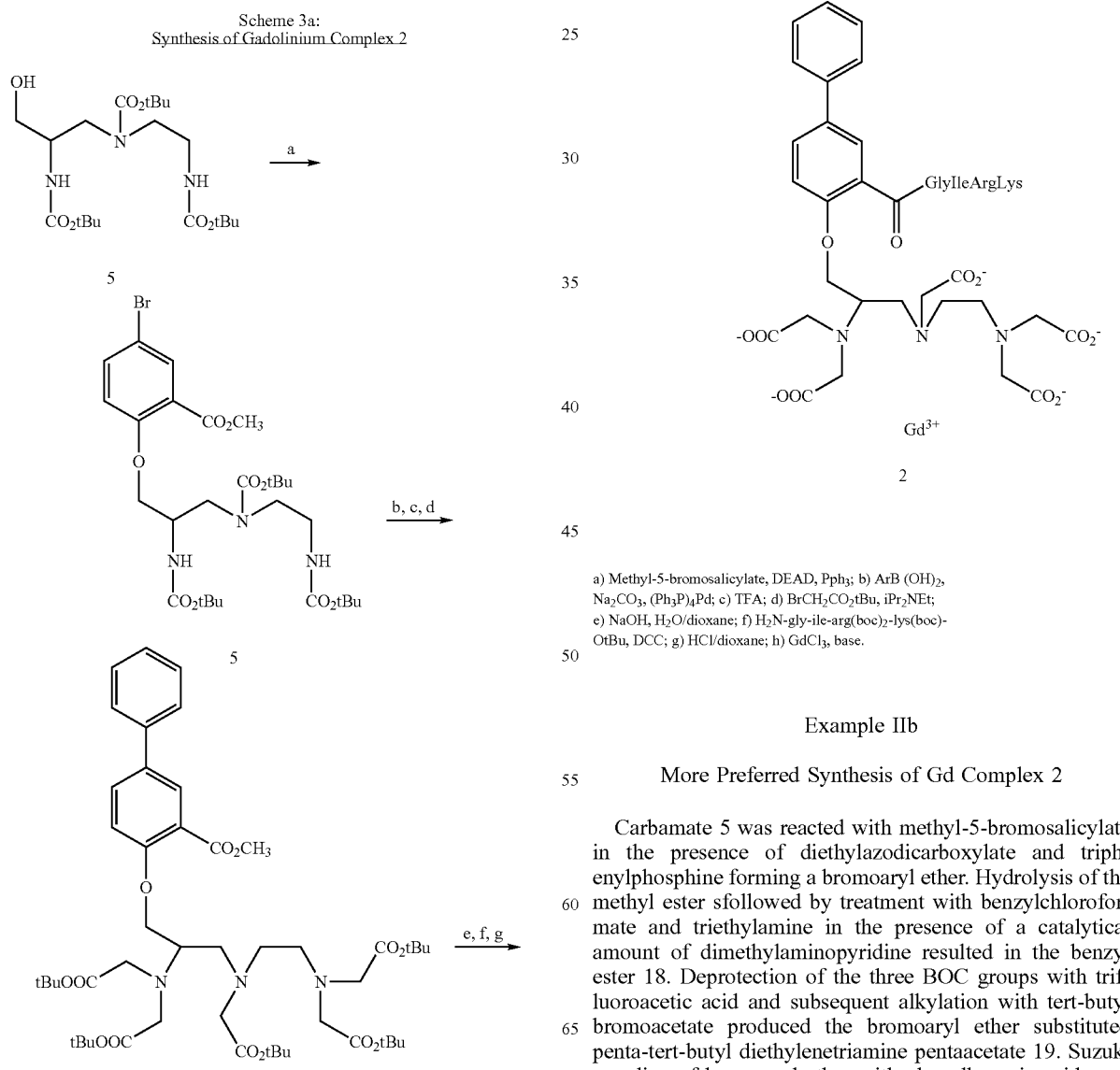

a) Methyl-5-bromosalicylate, DEAD, Pph$_3$; b) ArB (OH)$_2$, Na$_2$CO$_3$, (Ph$_3$P)$_4$Pd; c) TFA; d) BrCH$_2$CO$_2$tBu, iPr$_2$NEt; e) NaOH, H$_2$O/dioxane; f) H$_2$N-gly-ile-arg(boc)$_2$-lys(boc)-OtBu, DCC; g) HCl/dioxane; h) GdCl$_3$, base.

Example IIb

More Preferred Synthesis of Gd Complex 2

Carbamate 5 was reacted with methyl-5-bromosalicylate in the presence of diethylazodicarboxylate and triphenylphosphine forming a bromoaryl ether. Hydrolysis of the methyl ester sfollowed by treatment with benzylchloroformate and triethylamine in the presence of a catalytical amount of dimethylaminopyridine resulted in the benzyl ester 18. Deprotection of the three BOC groups with trifluoroacetic acid and subsequent alkylation with tert-butyl bromoacetate produced the bromoaryl ether substituted penta-tert-butyl diethylenetriamine pentaacetate 19. Suzuki coupling of bromoaryl ether with phenylboronic acid gave the biphenyl ether. Hydrogenolysis of benzylester in the presence of palladium catalyst gave the biphenylcarboxylate 20. Coupling of 20 with benzyl glycinate followed by the hydrogenolysis of the benzyl ester gave the amide 21. Coupling of 21 with the protected tripeptide, H$_2$N-Ile-Arg (BOC)$_2$-Lys(BOC)-OtBu, using dicyclohexylcarbodiimide in DMF and subsequent deprotection of the t-butyl esters and the BOC groups with TFA resulted in the tetrapeptide 22. Reaction with GdCl$_3$ in the presence of sodium hydroxide gave complex 2 which is purified by reverse-phase HPLC (Scheme 3b).

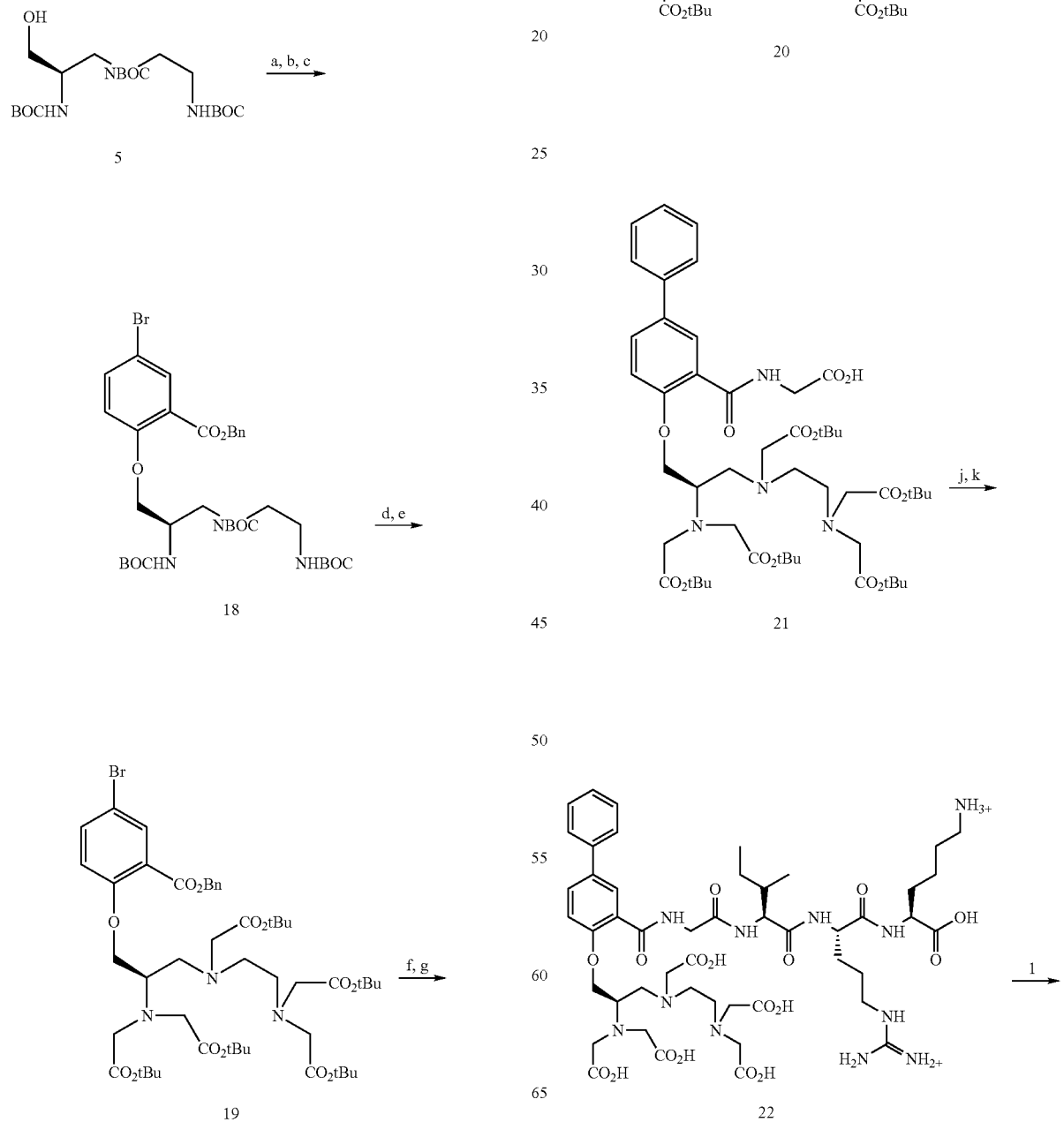

-continued

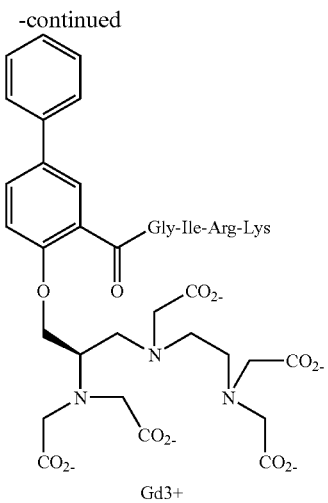

2 a) Methyl-5-bromosalicylate, DEAD, PPh₃, THF; b) 2N KOH (aq), MeOH; c) ClCO₂Bn, Et₃N, DMAP, CH₂Cl₂; d) TFA;
e) BrCH₂CO₂tBu, i-Pr₂NEt, DMF; f) Ph—B(OH)₂, (Pph₃)₄Pd, Na₂CO₃, Toluene, MeOH, H₂O, Δ; g) H₂, Pd, C, MeOH; h) H₂NCH₂CO₂Bn, DCC, CH₂Cl₂; I) H₂, Pd, C, MeOH; j) H₂N-113-Arg(BOC)₂-Lys(BOC)-OtBu, DCC, HOBt, DMF; k) TFA;
i) GdCl₃, NaOH.

Example IIIa

Activation of Prodrug Compound 1

Prodrug 1 is activated by alkaline phosphate as shown below. Activated contrast agent 8, produced by hydrolysis of the MS (phosphorous-oxygen bond), binds at a concentration of 0.1 mM to HSA with greater affinity than prodrug 1. The increased relativity results from a shortening of $T_1$, which is detected as an increase in signal intensity in an MRI image.

Activation of Prodrug Compound 1

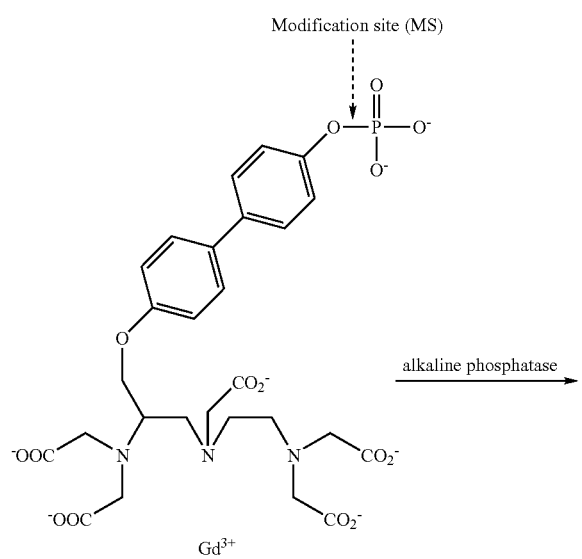

-continued

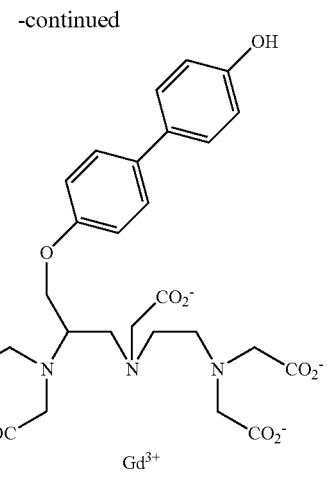

8

Example IIIb

More Preferred Activation of Prodrug Compound 1

Compound 1 (see Examples Ib and IIIa) was synthesized as described in Example Ib. Prodrug 1 was activated by alkaline phosphatase (see Example IIIa⁻ Activation of Prodrug 1) which hydrolyses the MS (phosphorus-oxygen bond), forming activated contrast agent 8. Compound 8 bound at a concentration of 0.1 mM to HSA with greater affinity than prodrug 1 and with a higher relaxivity. The higher relaxivity resulted from a shortening of $T_1$, which was detected as an increase in signal intensity in an MRI image (See Table V below).

TABLE V

Relaxivity and Percent Binding to HSA

| Compound | Relaxivity in 4.5% HSA | Percent Binding in 4.5% HSA |
|---|---|---|
| 1 | 15.9 ± 0.2 | 47 ± 1 |
| 8 | 26.4 ± 0.4 | 63 ± 2 |

In Table V, the longitudinal relaxivities ($R_1$) were obtained at 20 MHz and 37° C. by determining the concentration dependent relaxation rate ($1/T_1$) of water protons in phosphate buffered saline (PBS, 150 mM NaCl, 10 mM phosphate, pH=7.4) or in PBS solutions containing 4.5% human serum albumin (HSA). The percent bound to HSA was determined by ultrafiltration of a 0.1 mM chelate, 4.5% HSA solution.

A solution of prodrug 1 (0.3 mM) was prepared in PBS buffer (pH 7) containing 4.5% HSA. No change in the 20 MHz proton relaxation rate $1/T_1$ was observed with time. Three units of alkaline phosphatase (1 unit converts 1 nmol of p-nitrophenylphosphate to p-nitrophenol per minute in phosphate buffered saline at 0.1 mM substrate) were added to the 4.5% HSA solution of compound 1 and the $1/T_1$ was monitored over time. The $1/T_1$ for the solution was observed to change as −1 was enzymatically converted to 8 (Table VI). Upon completion of enzymatic activation of 1 to 8, the change in $1/T_1$ from time zero was 2.86 $sec^{-1}$, which corresponds to an approximate expected increase in signal intensity of 24%.

TABLE VI

Bioactivation of Prodrug 1 at 20 MHz

| Time (min) | 1/T1 ($sec^{-1}$) |
|---|---|
| 0 | 4.440 |
| 1 | 4.348 |
| 2 | 4.651 |
| 4 | 4.878 |
| 6 | 5.025 |
| 14 | 5.376 |
| 48 | 6.250 |
| 90 | 6.849 |
| 110 | 7.042 |
| 137 | 7.299 |

Solutions of 4.5% HSA containing compounds 1 and 8 (0.1–0.2 mM) were prepared. After 15 minutes, an initial T1-weighted MRI scan (FISP-3D, TR=60, TE=5, alpha=60) at 1.0 Tesla of the 4.5% HSA solutions was obtained. The MRI scans of the solutions containing 8 were brighter than the solutions containing 1 at equivalent concentrations. Three units of alkaline phosphatase were added to half of the HSA solutions containing 1 and additional T1-weighted MRI scans were obtained. After 130 minutes, the solutions that contained 1 and alkaline phosphatase obtained 96% of the signal intensity that for the solutions that contain 8 at equivalent concentrations. The solutions that contained 1 without alkaline phosphatase remained as constant dark images during the MRI scans. A 20% increase in signal intensity was observed after addition of alkaline phosphatase to solutions containing 1.

Example IV

Activation of Gadolinium Complex 2

Prodrug a containing a hydrophilic isoleucine-arginine-lysine side chain MM is activated by collegenase (MMP-1). The MS is a carbon-nitrogen peptide bond which is selectively hydrolyzed by MMP-1 (gly-ile). Release of the ile-arg-lys MM generates compound 9, which is characterized by higher binding affinity for HSA than the prodrug 2. The altered signal in the MRI permits the bioactivity to be imaged.

Activation of Gadolinium Complex 2

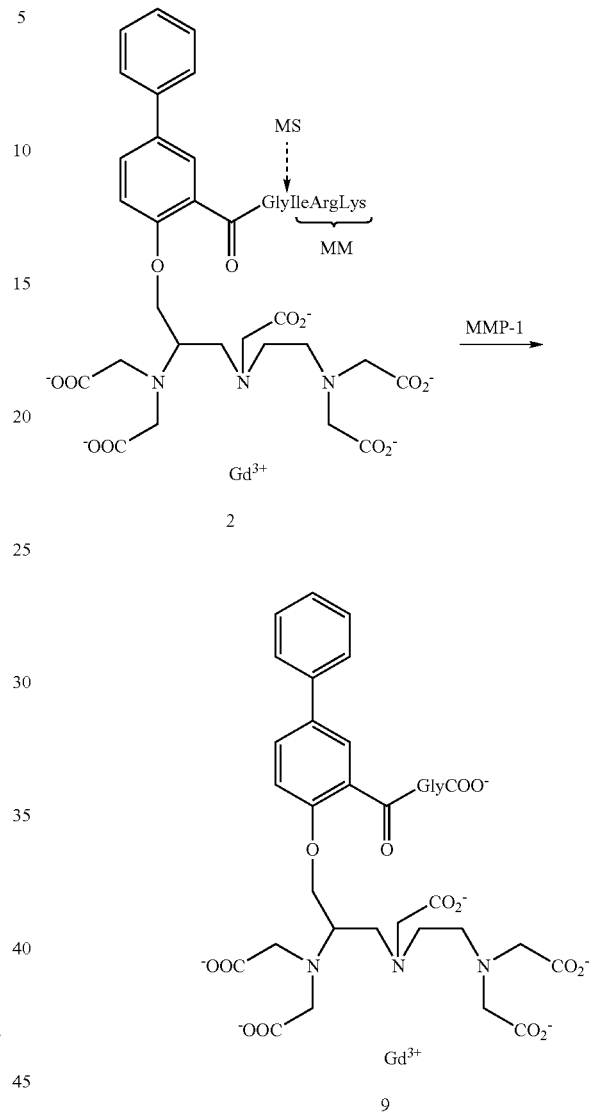

Example V

Activation of Gadolinium Complex 10

This example also shows how a secondary chemical reaction is coupled to a primary bioactivity-related event. Prodrug 10 containing an MM composed of the tripeptide tmLys-tmLys-Arg (where tmLys is Nε, Nε, Nε-trimethyl-ysine) is activated by serine protease. The MS is the Arg-Glu carbon-nitrogen peptide bond which is cleaved by serine proteinase enzymatic bioactivity to release the masking moiety. The enzymatic hydrolysis to give intermediate compound 11 is followed by a secondary chemical reaction (intramolecular cyclization) with an aliphatic or activated ester (e.g., R=p-nitrophenyl). This converts the positively charged PBM moiety in 11 to the more lipophilic, more highly HSA-bound, neutral lactam derivative 12.

Activation of Prodrug Compound 10

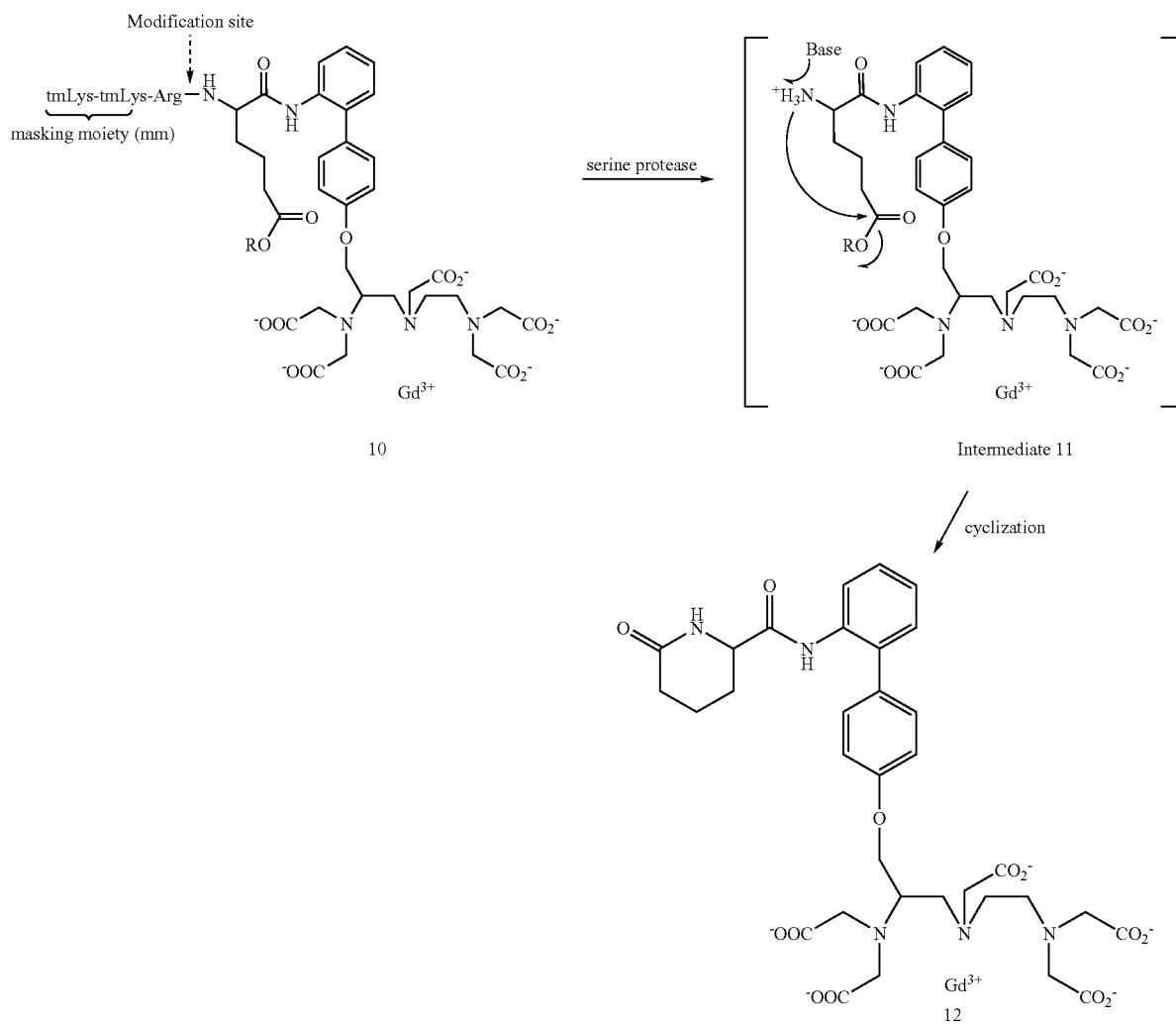

Example VI

Administration of Prodrug Contrast Agents

Prodrug compound 2, an MMP substrate, is synthesized by chemical and peptide techniques known in the art and described above. A pH 7.0 formulation in water is prepared and sterilized.

The formulation is injected intravenously into a patient suspected of having one or more tumors. The dosage used is 0.025 mmol/kg. After 15 minutes-post-injection, $T_1$-weighted MRI scans of the region of the body suspected to contain tumors is obtained. Masses that appear bright on the images are more likely to be malignant tumors than benign.

This same formulation is injected intravenously into a patient suspected of having rheumatoid arthritis in one or more joints. The dosage used is 0.025 mmol/kg. After 15 minutes post-injection, $T_1$-weighted MRI scans of the joints of the body suspected to contain arthritis is obtained. Joints that appear bright on the images are more likely to contain active inflammation.

This same formulation is injected intravenously into a patient with atherosclerosis in one or more arteries. The dosage used is 0.025 mmol/kg. After 15 minutes post-injection, $T_1$-weighted MRI scans (cross-sectional scans or MR angiography) of the arteries is obtained. Atherosclerotic plaque that enhances brightly is more likely to be unstable plaque, likely to rupture and cause ischemia to the organ the artery feeds.

We claim:
1. A composition of matter having the following formula: IEM-PBM-[L]-[MS-MM]$_p$,
   wherein p is 1;
   wherein L comprises a physiologically compatible linker moiety which links the PBM and [MS-MM] moieties;
   wherein said IEM comprises a complex between:
   (1) a chelating agent selected from the group consisting of DTPA, DOTA, DTPA-BMA, and HP-DO3A, and
   (2) one or more paramagnetic metal ions (M) with atomic numbers 21–29, 42, 44, or 57–83;
   wherein said -PBM moiety is selected from the group consisting of:

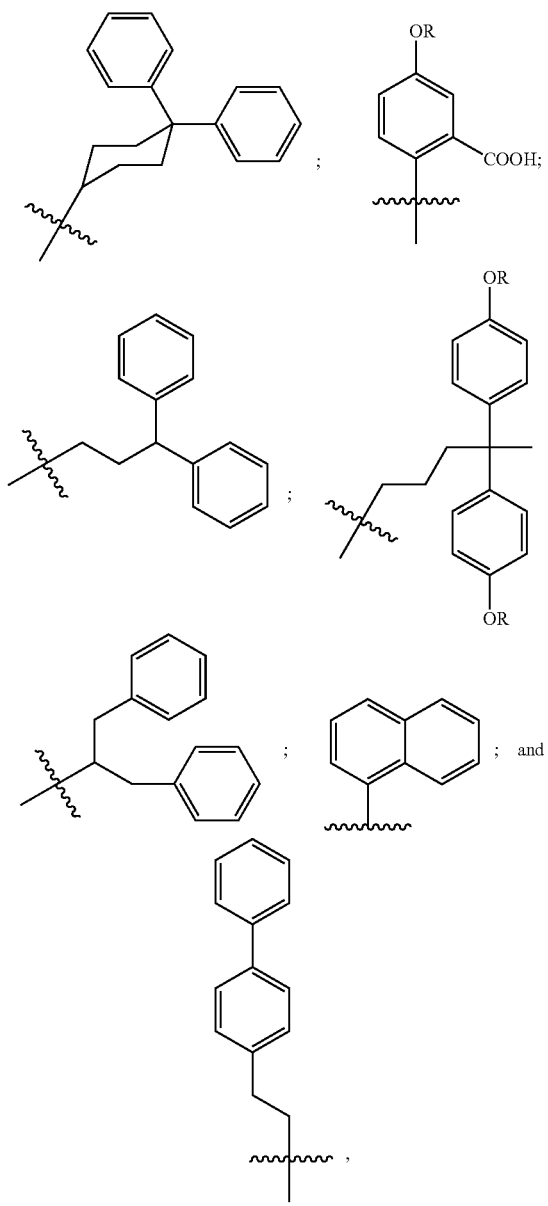

wherein one aryl ring of said -PBM is substituted with said -[L]-[MS-MM]$_p$ moiety;
wherein R is selected from the group consisting of aliphatic group, an aryl group, or a cycloalkyl group;
wherein the wavy line signifies the attachment site for the IEM;
wherein said -PBM moiety is conjugated to said IEM via a covalent bond to a methylene carbon of said chelating agent of said IEM;
wherein said MS moiety is an amide bond;
wherein said MM moiety is a peptide consisting of two or three amino acids;
and pharmaceutically acceptable salts thereof.

2. The composition of claim 1, wherein said MM moiety is a peptide consisting of two Arg, Lys, or tm-Lys amino acids, or mixtures thereof.

3. The composition of claim 1, wherein said MM moiety is -Arg-tmLys-tmLys.

4. The composition of claim 1, wherein said MM moiety is Ile-Arg-Lys.

5. The composition of claim 1, wherein said chelating agent is selected from the group consisting of:

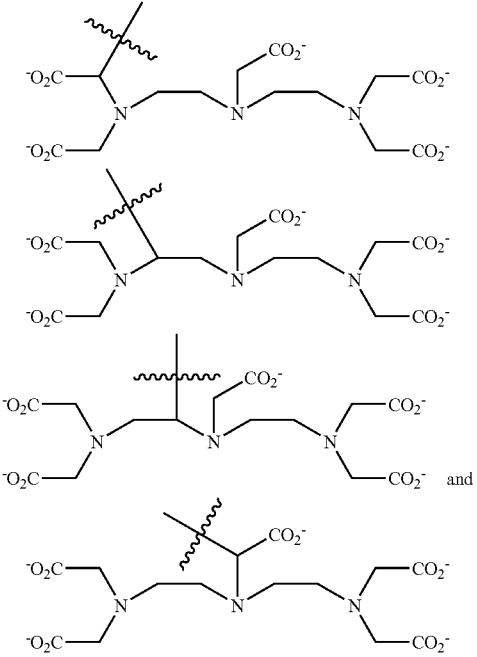

wherein the wavy line signifies the attachment site for the -PBM-L-MS-MM moiety.

6. The composition of claim 1, wherein said chelating agent is

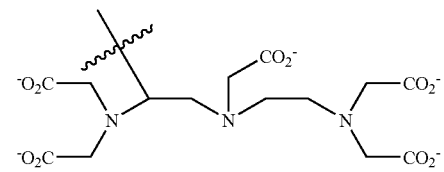

wherein the wavy line signifies the attachment site for the -PBM-L-MS-MM moiety.

7. The composition of claim 1, wherein said paramagnetic metal ion is selected from the group consisting of:
(a) Gd (III),
(b) Mn (II),
(c) Fe (III),
(d) Cu (II),
(e) Cr (III), and
(f) Eu (III).

8. The composition of claim 7, wherein said paramagnetic metal ion is Gd(III).

9. The composition of claim 1, wherein the pharmaceutically acceptable salt is an N-methyl-D-glucamine, calcium, or sodium salt.

10. The composition of claim 9, wherein the pharmaceutically acceptable salt is a sodium salt.

11. A composition of matter having the following structure:

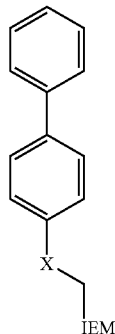

wherein said IEM comprises a complex between:
(1) a chelating agent selected from the group consisting of DTPA, DOTA, DTPA-BMA, and HP-DO3A, and
(2) one or more paramagnetic metal ions (M) with atomic numbers 21–29, 42, 44, or 57–83;
wherein one aryl ring of said structure is substituted with a L-[MS-MM]$_p$ moiety, wherein p is one;
wherein X is $CH_2$, O, or NH;
wherein L comprises a physiologically compatible linker moiety which links said one substituted aryl ring with said -[MS-MM]$_p$ moiety;
wherein said MS moiety is an amide bond;
wherein said MM moiety is a peptide consisting of two or three amino acids;
and pharmaceutically acceptable salts thereof.

12. The composition of claim 11, wherein said MM moiety is a peptide consisting of two Arg, Lys, or tm-Lys amino acids, or mixtures thereof.

13. The composition of claim 11, wherein said MM moiety is -Arg-tmLys-tmLys.

14. The composition of claim 11 wherein said MM moiety is Ile-Arg-Lys.

15. The composition of claim 11, wherein said chelating agent is selected from the group consisting of:

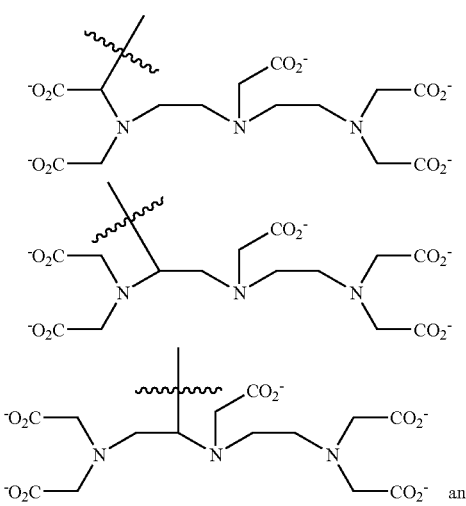

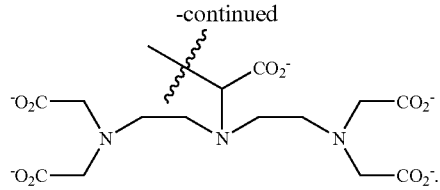

16. The composition of claim 15, wherein said chelating agent is

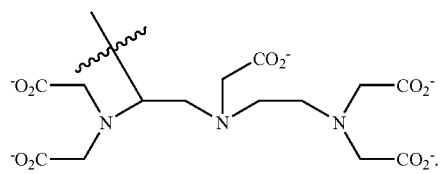

17. The composition of claim 11, wherein said paramagnetic metal ion is selected from the group consisting of:
(a) Gd (III),
(b) Mn (II),
(c) Fe (III),
(d) Cu (II),
(e) Cr (III), and
(f) Eu (III).

18. The composition of claim 17, wherein said paramagnetic metal ion is Gd(III).

19. The composition of claim 11, wherein the pharmaceutically acceptable salt is an N-methyl-D-glucamine, calcium, or sodium salt.

20. The composition of claim 19, wherein said pharmaceutically acceptable salt is a sodium salt.

21. A method for magnetic resonance imaging, said method comprising:
a) administering to a mammal the composition of matter of claim 1 or 11,
b) allowing the composition of matter to be bioactivated;
c) allowing said bioactivated composition of matter to bind to a protein on the extracellular surface of a tissue or in extracellular fluid surrounding a tissue, said tissue containing a bioactivity to be detected; and
d) subjecting said mammal to magnetic resonance imaging.

22. A compound having the structure of Prodrug Compound 2:

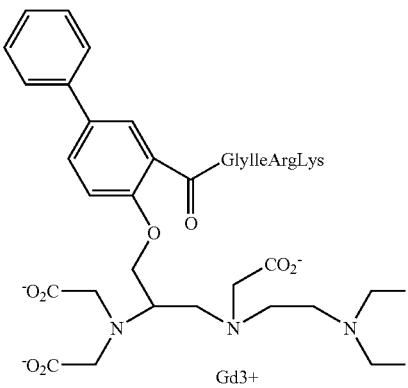

or Prodrug Compound 10:
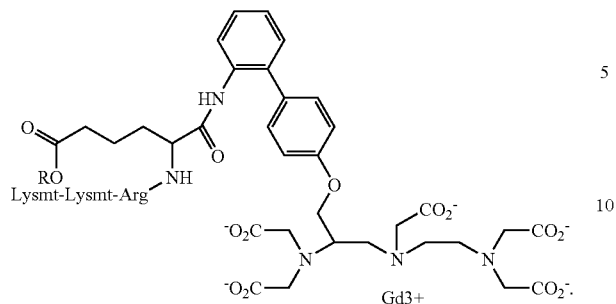
23. The composition of claim 1 or 11, wherein said L moiety is a peptoid linkage.
24. The composition of claim 1 or 11, wherein said L moiety has the following structure:
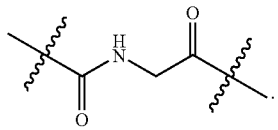
* * * * *